US011266729B2

(12) United States Patent
Tsunoda et al.

(10) Patent No.: US 11,266,729 B2
(45) Date of Patent: Mar. 8, 2022

(54) UBE2T PEPTIDES AND VACCINES CONTAINING THE SAME

(71) Applicant: OncoTherapy Science, Inc., Kanagawa (JP)

(72) Inventors: Takuya Tsunoda, Kanagawa (JP); Ryuji Osawa, Kanagawa (JP); Sachiko Yoshimura, Kanagawa (JP); Tomohisa Watanabe, Kanagawa (JP)

(73) Assignee: ONCOTHERAPY SCIENCE, INC., Kawasaki (JP)

( * ) Notice: Subject to any disclaimer, the term of this patent is extended or adjusted under 35 U.S.C. 154(b) by 677 days.

(21) Appl. No.: 16/120,102

(22) Filed: Aug. 31, 2018

(65) Prior Publication Data
US 2018/0360938 A1 Dec. 20, 2018

Related U.S. Application Data

(62) Division of application No. 14/400,169, filed as application No. PCT/JP2013/005321 on Sep. 9, 2013, now Pat. No. 10,092,634.

(60) Provisional application No. 61/699,550, filed on Sep. 11, 2012.

(51) Int. Cl.
A61K 39/00 (2006.01)
C12N 5/0783 (2010.01)
C12N 5/078 (2010.01)
C07K 16/40 (2006.01)
A61K 31/7088 (2006.01)
C12N 9/00 (2006.01)
G01N 33/574 (2006.01)

(52) U.S. Cl.
CPC .. A61K 39/001154 (2018.08); A61K 31/7088 (2013.01); C07K 16/40 (2013.01); C12N 9/93 (2013.01); C12Y 603/02019 (2013.01); G01N 33/57492 (2013.01); A61K 2039/5154 (2013.01)

(58) Field of Classification Search
None
See application file for complete search history.

(56) References Cited

U.S. PATENT DOCUMENTS

2007/0202109 A1 8/2007 Nakamura et al.
2010/0273855 A1 10/2010 Togashi et al.

FOREIGN PATENT DOCUMENTS

| CN | 1315998 A | 10/2001 |
|---|---|---|
| CN | 1323217 A | 11/2001 |
| CN | 1333830 A | 1/2002 |
| CN | 101796184 A | 8/2010 |
| CN | 102215870 A | 10/2011 |
| CN | 102459314 A | 5/2012 |
| EP | 1306431 A | 5/2003 |
| EP | 2340851 A1 | 7/2011 |
| JP | 2010-531133 A | 9/2010 |
| JP | 2012-510794 A | 5/2012 |
| JP | 2012-513742 A | 6/2012 |
| RU | 2009/135020 A | 3/2011 |
| WO | 2000/04149 A2 | 1/2000 |
| WO | 2000/20027 A2 | 4/2000 |
| WO | 2000/36107 A2 | 6/2000 |
| WO | 2005/029067 A2 | 3/2005 |
| WO | 2008/102557 A | 8/2008 |
| WO | 2008/102906 A1 | 8/2008 |
| WO | 2009/001562 A1 | 12/2008 |
| WO | 2010/032696 A1 | 3/2010 |
| WO | 2010/064430 A1 | 6/2010 |
| WO | 2010/073551 A1 | 7/2010 |
| WO | 2010/131452 A1 | 11/2010 |
| WO | 2012/053200 A1 | 4/2012 |
| WO | 2012/053206 A1 | 4/2012 |
| WO | 2012/073459 A1 | 6/2012 |

OTHER PUBLICATIONS

HLA Nomenclature 2015 (Year: 2015).*
Wieczorek et al (Front. Immunol. 2017, vol. 8, article 292: 1-16) (Year: 2017).*
Liu et al (MHC Complex: Interaction with Peptides. IN: eLS. John Wiley & Sons, Ltd: Chichester, DOI: 10.1002/9780470015902. a0000922.pub2, 2011, pp. 1-12) (Year: 2011).*
Engelhard, V.H. (Curr. Opin. Immunol. 1994, 6: 13-23) (Year: 1994).*
Eisenlohr et al (J. Exp. Med. 1992, 175: 481-487) (Year: 1992).*
Wang et al (Cell. Immunol. 1992, 143: 284-297) (Year: 1992).*
Perkins et al (J. Immunol. 1991, 146(7): 2137-2144) (Year: 1991).*
Theoboald et al (J. Exp. Med. 1998, 188(6): 1017-1028) (Year: 1998).*
Gileadi et al (Eur. J. Immunol. 1999, 29: 2213-2222) (Year: 1999).*
Ochoa-Garay et al (Mol. Immunol. 1997, 34(3): 273-281) (Year: 1997).*

(Continued)

Primary Examiner — Michael Szperka
Assistant Examiner — Marianne DiBrino
(74) Attorney, Agent, or Firm — Kilpatrick Townsend & Stockton LLP

(57) ABSTRACT

Peptide vaccines against cancer are described herein. In particular, epitope peptides derived from the UBE2T that CTLs are provided. Isolated antigen-presenting cells with CTL inducibility and CTLs that target such peptides, as well as methods for inducing the antigen-presenting cell, or CTL are also provided. The present invention further provides pharmaceutical compositions containing such epitope peptides derived from UBE2T or polynucleotides encoding the polypeptides as active ingredients. Furthermore, the present invention provides methods for the treatment and/or prophylaxis of (i.e., preventing) cancers (tumors), and/or the prevention of a postoperative recurrence thereof, as well as methods for inducing CTLs, methods for inducing anti-tumor immunity, using the epitope peptides derived from UBE2T, polynucleotides encoding the peptides, or antigen-presenting cells presenting the peptides, or the pharmaceutical compositions of the present invention.

3 Claims, 8 Drawing Sheets
Specification includes a Sequence Listing.

(56) References Cited

OTHER PUBLICATIONS

Shastri et al (J. Immunol. 1995, 155: 4339-4346) (Year: 1995).*
Bergmann et al (J. Immunol. 1996, 157: 3242-3249) (Year: 1996).*
Beatty and Gladney (Clin. Canc. Res. 2014, 21(4): 687-692) (Year: 2014).*
Berger et al (Int. J. Cancer. 111: 229-237, 2004) (Year: 2004).*
Kalos and June (Immunity, 2013, 39: 49-60 (Year: 2013).*
Spranger, S (Int. Immunol. 2015, 28(8): 383-391) (Year: 2015).*
Kerkar and Restifo (Cancer Res.2012, 72(13): 3125-3130) (Year: 2012).*
Celis et al (PNAS USA, 1994, 91: 2105-2109) (Year: 1994).*
Knutson et al (Clin. Canc. Res. 2002, 8: 1014-1018) (Year: 2002).*
Engelhard, V.H. (Curr. Opin. Immunol. 1994, 6: 13-23).
Guo et al (Nature, 1992, 360: 364-366).
Celis et al (PNAS USA, 1994, 91: 2105-2109).
Ochoa-Garay et al (Mol. Immunol. 1997, 34(3): 273-281).
HLA Nomenclature 2015.
Fournier and Schirrmacher (Expert. Rev. Vaccines 8(1 ); 51-66, 2009).
Schrieber et al (Seminar. Immunol. 22: 105-112, 2010).
Klebanoff et al (Immunol. Rev. 2011, 239: 27-44).
Rammensee et al (MHC Ligands and Peptide Motifs, 2017, Landes Bioscience, Austin TX, Springer, NY, pp. 237 and 239).
Wen, et al., "Elevated Expression of UBE2T Exhibits Oncogenic Properties in Human Prostate Cancer," Oncotarget, vol. 6, No. 28, (2015) pp. 25226-25239.
Gu, Database of Thesis for Doctor's Degree in China, Basic Sciences Volume, Mar. 15, 2009, A006-31 (English Abstract included).
Genbank Accession No. AAY01707.1, Apr. 20, 2005.
Genbank Accession No. ACK00306.1, Dec. 10, 2008.
DDBJ Accession No. DJ518199, Aug. 24, 2012.
PDB Accession No. 1YH2, Jan. 6, 2005.
UniProtKB Accession No. F7E3Q2, Jul. 27, 2011.
Lee et al., "Increased Vaccine-Specific T Cell Frequency After Peptide-Based Vaccination Correlates with Increased Susceptibility to In Vitro Stimulation but Does Not Lead to Tumor Regression," The Journal of immunology, 1999, 163: 6292-6300.
Pinilla-Ibarz, et al., "Synthetic Peptide Analogs Derived from bcr/abl Fusion Proteins and the Induction of Heteroclitic Human T-Cell Responses," Haematologica, Oct. 2005, 90⊕10): 1324-32.
Ibe et al., "Role of Strong Anchor Residues in the Effective Binding of 10-mer and 11-mer Peptides to HLA-A*2402 Molecules," Immunogenics (1996) 44:233-241.
Stevanovic, "Identification of Tumour-Associated T-Cell Epitopes for Vaccine Development," Nature Reviews, Cancer, vol. 2, Jul. 2002, pp. 1-7.
Adams, et al., "Prediction of binding to MHC class I molecules", J Immunol Methods, vol. 185, No. 2, pp. 181-190 (1995).
Alpi et al., "UBE2T, the Fanconi Anemia Core Complex, and FANCD2 Are Recruited Independently to Chromatin: a Bases for the Regulation of FANCD2 Monoubiquitination", Molecular and Cellular Biology, vol. 27, No. 24, pp. 8421-8430 (2007).
Belli, et al., "Vaccination of Metastatic Melanoma Patients with Autologous Tumor-Derived Heat Shock Protein gp96-Peptide complexes: Clinical and Immunologic Findings", J Clin Oncol., vol. 20, No. 20, pp. 4169-4180 (2002).
Boon, "Tumor Antigens Recognized by Cytolytic T Lymphocytes: Present Perspectives for Specific Immunotherapy," Int J Cancer, vol. 54(2), pp. 177-180 (1993).
Boon T., et al., "Human Tumor Antigens Recognized by T Lymphocytes," J Exp Med., vol. 183(3), pp. 725-729 (1996).
Butterfield, et al., "Generation of Human T-Cell Responses to an HLA-A2.1-restricted Peptide Epitope Derived from α-Fetoprotein," Cancer Res., vol. 59, No. 13, pp. 3134-3142 (1999).
Coulie, et al., "Cytolytic T-cell Responses of cancer patients vaccinated with a MAGE antigen", Immunol Rev., vol. 188, pp. 33-42.
Dionne, et al., "Functional characterization of CTL against gp100 altered peptide ligands", Cancer Immunol Immunother. vol. 52, No. 4, pp. 199-206 (2003).

Dionne, et al., "Her-2/neu altered peptide ligand-induced CTL responses: implications for peptides with increased HLA affinity and T-cell-receptor interaction", Cancer Immunol Immunother. vol. 53, No. 4, pp. 307-314 (2004).
Falk, et al., "Allele-specific motifs revealed by sequencing of self-peptides eluted from MHC molecules", Nature, vol. 351, No. 6324, pp. 290-296 (1991).
Fujie, et al., "A Mage-1-Encoded HLA-A24-Binding Synthetic Peptide Induces Specific Anti-tumor Cytotoxic T Lymphocytes", Int. J. Cancer., vol. 80, No. 2, pp. 169-172 (1999).
Hao et al., "Elevated Expression of UBE2T in Lung Cancer Tumors and Cell Lines", Tumor Biology, vol. 29, No. 3, pp. 195-203 (2008).
Harris, "Structure and Function of the p53 Tumor Suppressor Gene: Clues for Rational Cancer Therapeutic Strategies," J Natl Cancer Inst., vol. 88(20), pp. 1442-1455 (1996).
Hoffman, et al., "The Ability of Variant Peptides to Reverse the Nonresponsiveness of T Lymphocytes to the Wild-Type Sequence $p53_{264-272}$ Epitope," J Immunol, vol. 168, No. 3, pp. 1338-1347 (2002).
Iyer et al., "The Transcriptional Program in the Response of Human Fibroblasts to Serum", Science, vol. 283, No. 5398, pp. 83-87 (1999).
Kikuchi, et al., "Identification of a Sart-1-Derived Peptide Capable of Inducing HLA-A24-Restricted and Tumor-Specific Cytotoxic T Lymphocytes", Int. J Cancer, vol. 81, No. 3, pp. 459-466 (1999).
Kondo, et al., "Prominent Roles of Secondary Anchor Residues in Peptide Binding to HLA-A24 Human Class I Molecules", J Immunol. vol. 155, No. 9, pp. 4307-4312 (1995).
Kubo, et al., "Definition of Specific Petptide Motifs for Four Major HAL-A Alleles", J Immunol, vol. 152, No. 8, pp. 3913-3924 (1994).
Machida et al., "UBE2T is the E2 in the Fanconi Anemia Pathway and Undergoes Negative Autoregulation", Molecular Cell, vol. 23, pp. 589-596 (2006).
Oiso, et al., "A Newly Identified Mage-3-Derived Epitope Recognized by HLA-A24-Restricted Cytotoxic T Lymphocytes", Int J Cancer, vol. 81, No. 3, pp. 387-394 (1999).
Parker, et al., "Scheme for Ranking Potential HLA-A2 Binding Peptides Based on Independent Binding of Individual Peptide Side-Chains", J Immunol., vol. 152, No. 1, pp. 163-175 (1994).
Rammensee, et al., "MHC ligands and peptide motifs: first listing," Immunogenetics, vol. 41(4), pp. 178-228 (1995).
Rosenberg, et al., "Cancer immunotherapy: moving beyond current vaccines", Nat. Med., vol. 10, No. 9, pp. 909-915 (2004).
Schueler-Furman, et al., "Structure-based prediction of binding peptides to MHC class I molecules: Application to a broad range of MHC alleles", Protein Sci., vol. 9, No. 9, pp. 1838-1846 (2000).
Tanaka, et al., "Induction of Antitumor Cytotoxic T Lymphocytes with a MAGE-3-encoded Synthetic Peptide Presented by Human Leukocytes Antigen-A24", Cancer Res., vol. 57, No. 20, pp. 4465-4468 (1997).
Ueki et al., "Ubiquitination and Downregulation of BRCA1 by Ubiquitin-Conjugating Enzyme E2T Overexpression in Human Breast Cancer Cells", Cancer Research, vol. 69, No. 22, pp. 8752-8760 (2009).
Van Der Burg, et al., "Immunogenicity of Peptides Bound to MHC Class I Molecules Depends on the MHC-Peptide Complex Stability," J. Immunol., vol. 156, No. 9, pp. 3308-3314 (1996).
Vissers, et al., "The Renal Cell Carcinoma-associated Antigen G250 Encodes a Human Leukocyte Antigen (HLA)-A2.1-restricted Epitope Recognized by Cytotoxic T Lymphocytes", Cancer Res., vol. 59, No. 21, pp. 5554-5559 (1999).
Zaremba, et al., "Identification of an Enhancer Agonist Cytotoxic T Lymphocytes Peptide from Human Carcinoembryonic Antigen", Cancer Res., vol. 57, No. 20, pp. 4570-4577 (1997).
International Search Report dated Dec. 3, 2013 for International Patent Application No. PCT/JP2013/005321, 3 pages.
GU; Database of Thesis for Doctor's Degree in China, Basic Sciences Volume, Mar. 15, 2009; A006-31; 3 pgs.; English Abstract only.

* cited by examiner

[Fig. 1a-l]
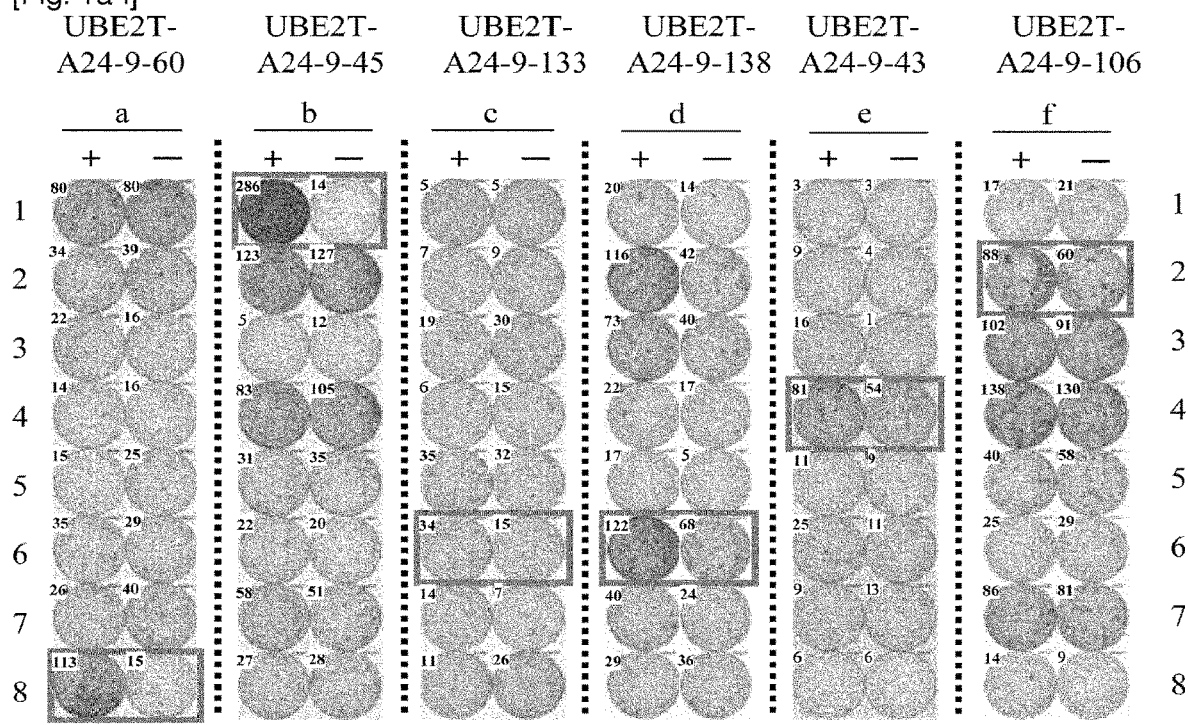
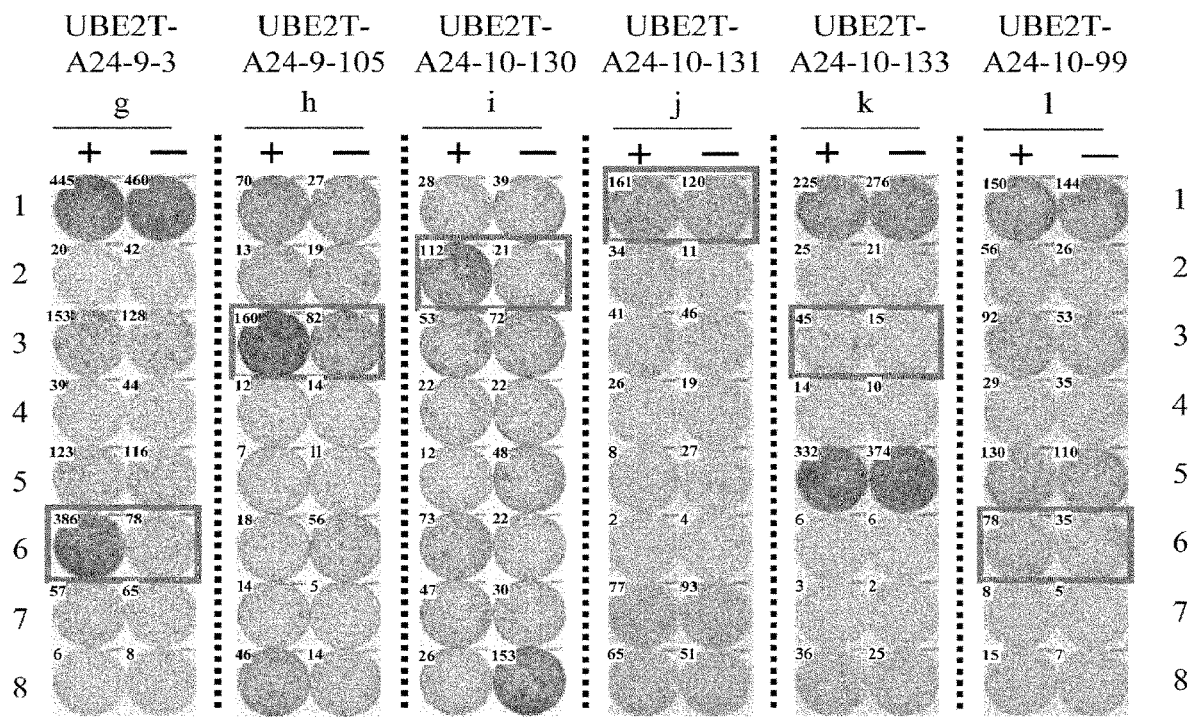

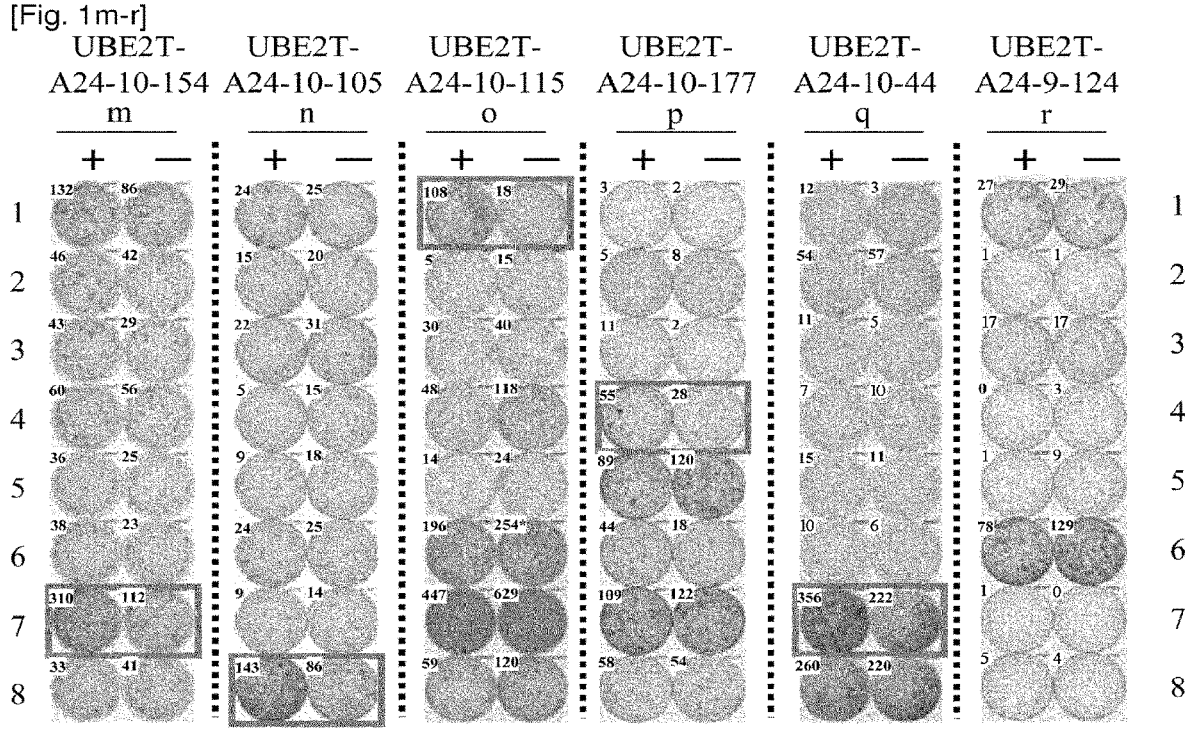
[Fig. 1m-r]

[Fig. 2a-l]
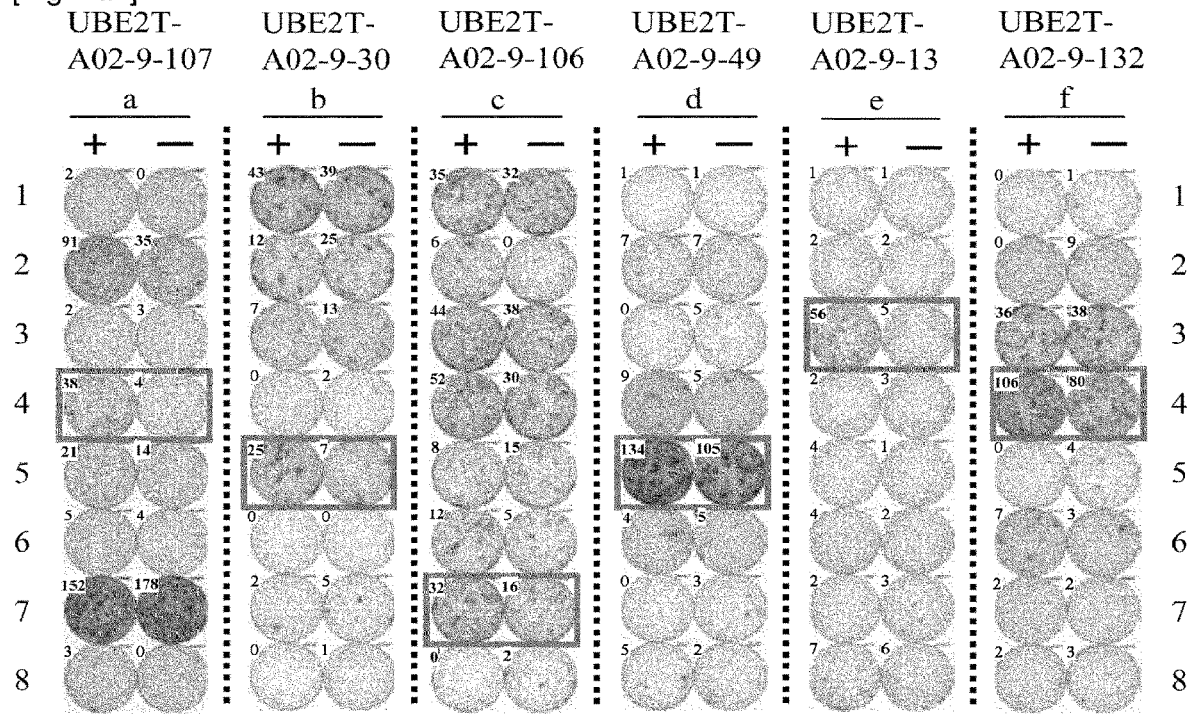
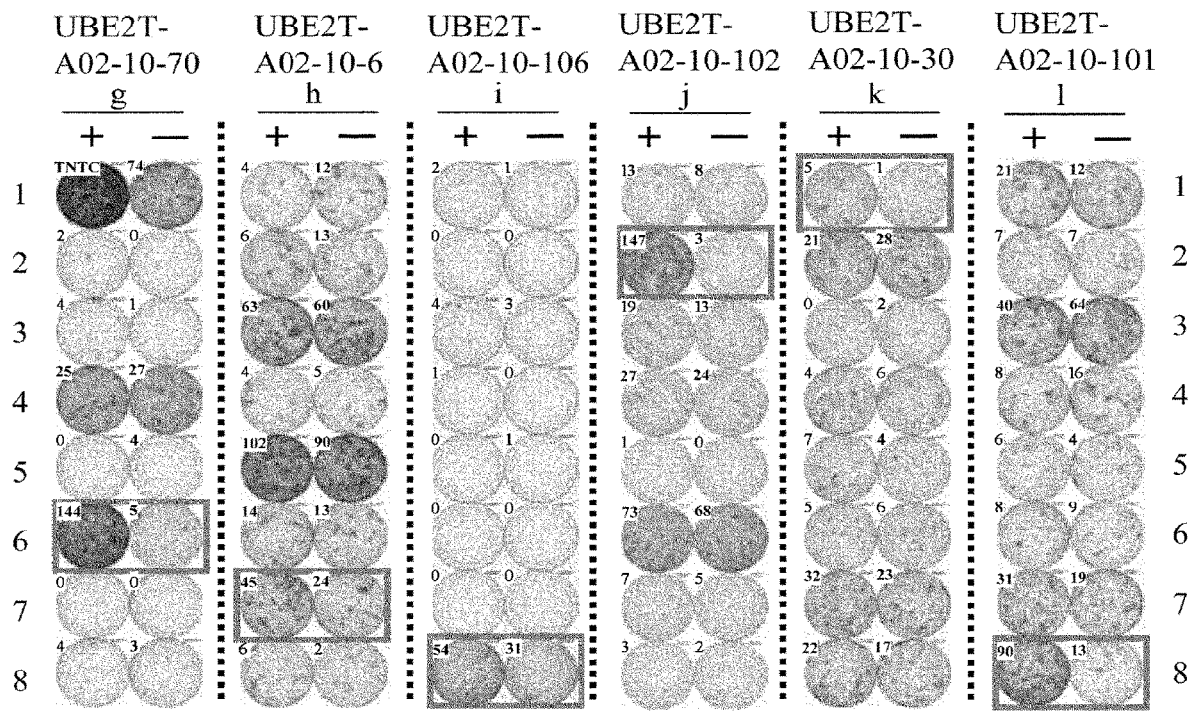

[Fig. 2m-o]
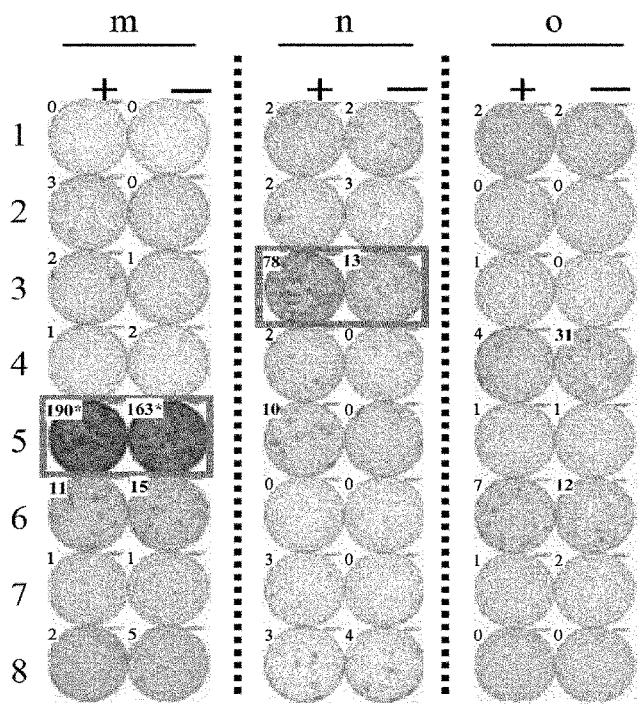
[Fig. 3]
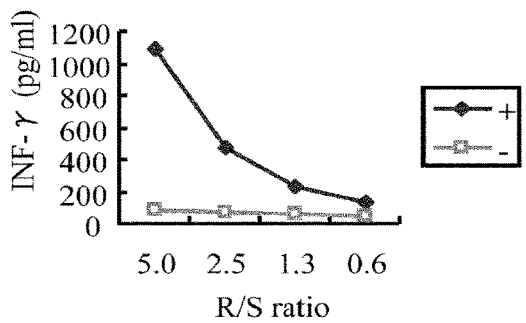
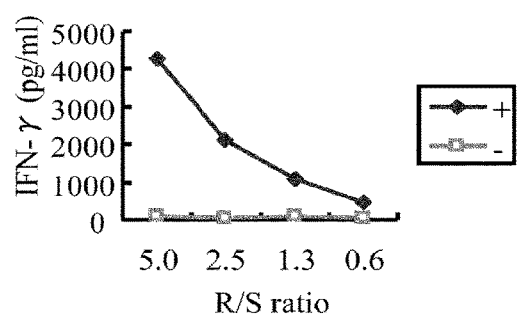
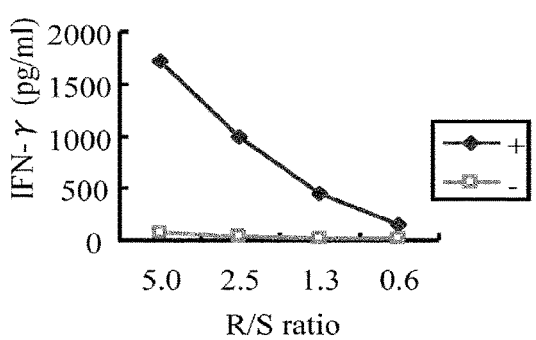
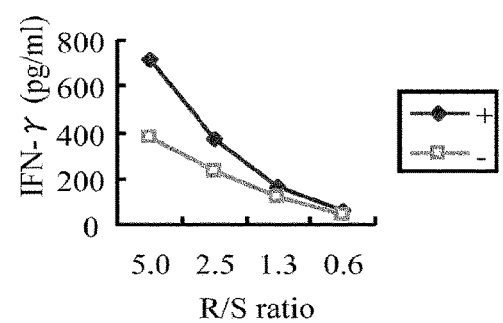

[Fig. 4]
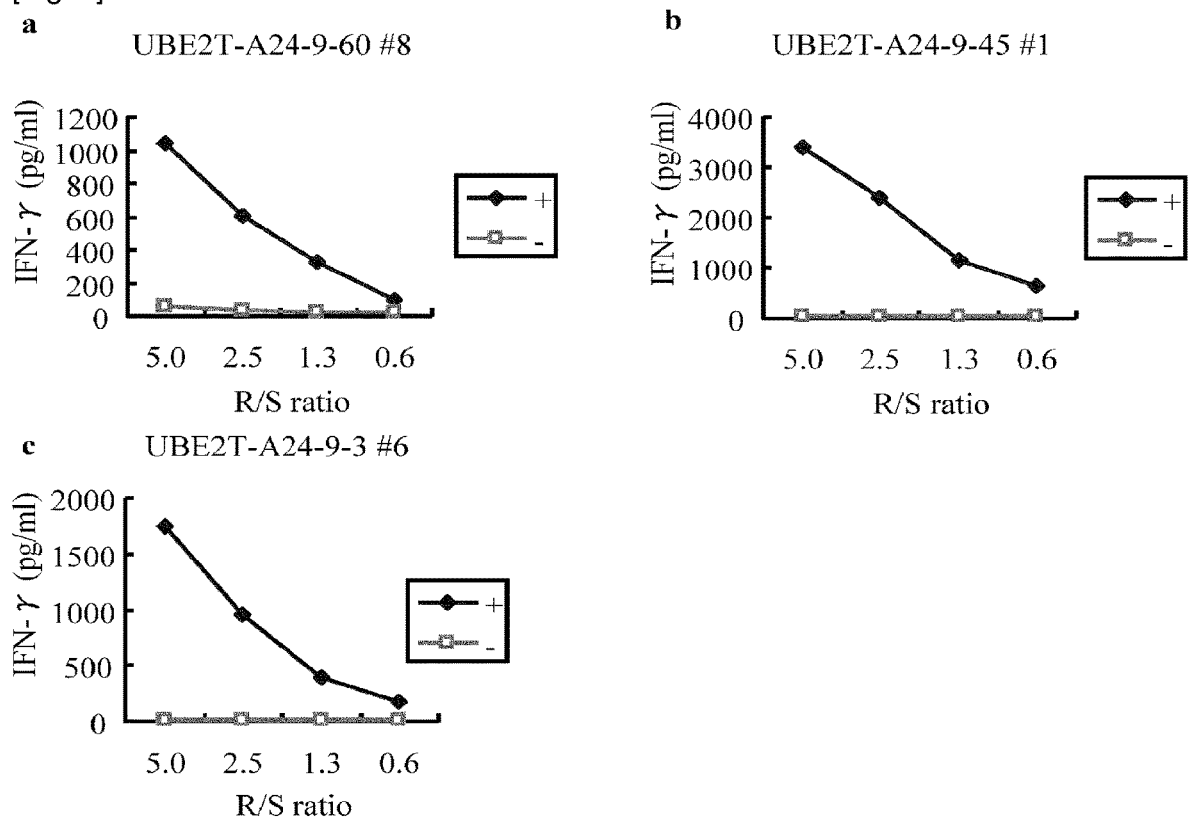

[Fig. 5]
a UBE2T-A02-9-107 #4
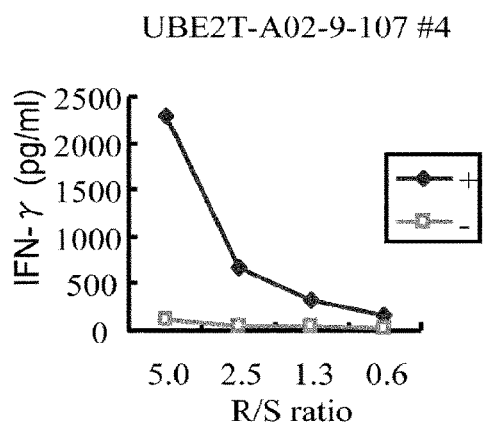
b UBE2T-A02-9-13 #3
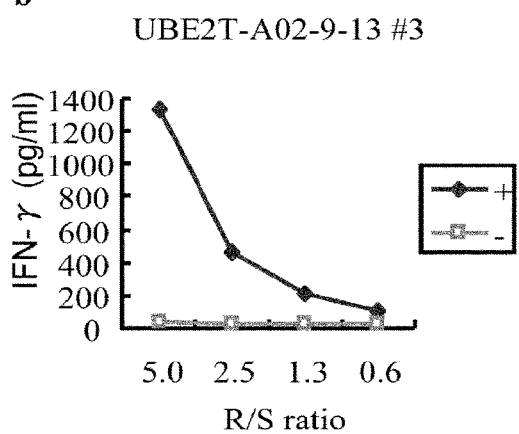
c UBE2T-A02-10-70 #6
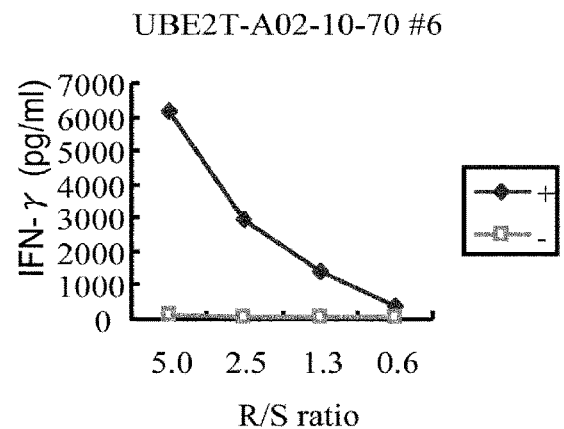
d UBE2T-A02-10-102 #2
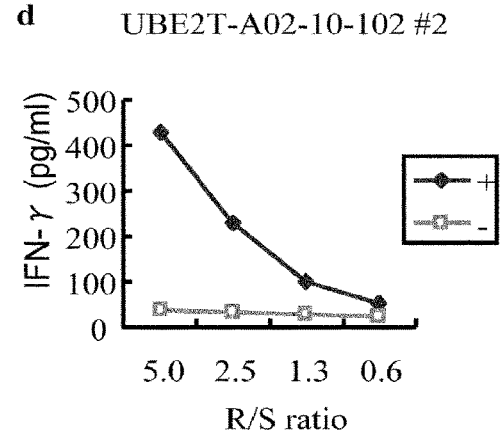
e UBE2T-A02-10-101 #8
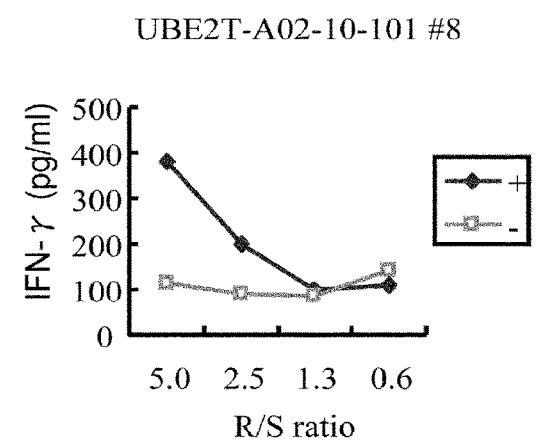

[Fig. 6]
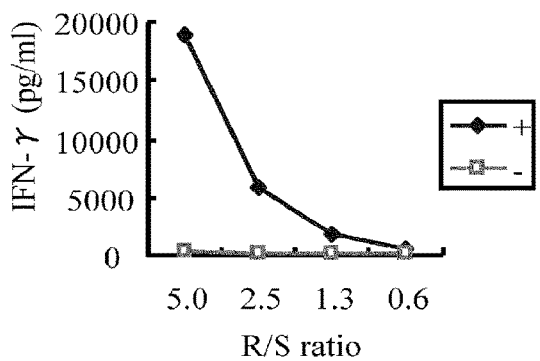
a  UBE2T-A02-9-107 #4
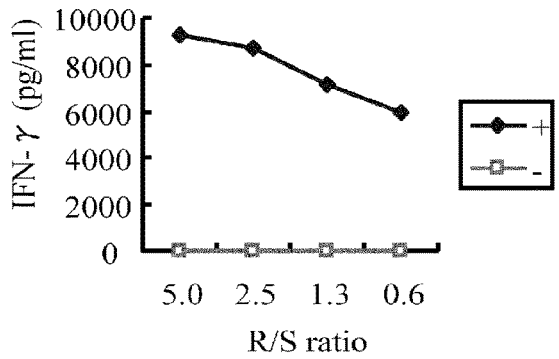
b  UBE2T-A02-9-13 #3
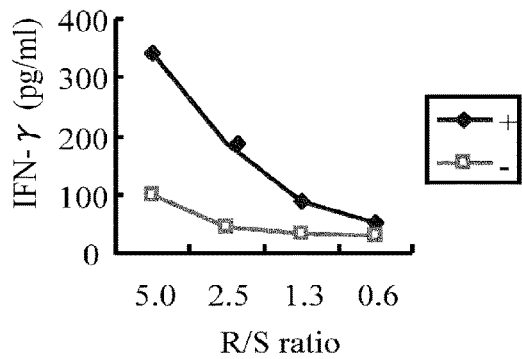
c  UBE2T-A02-10-70 #6
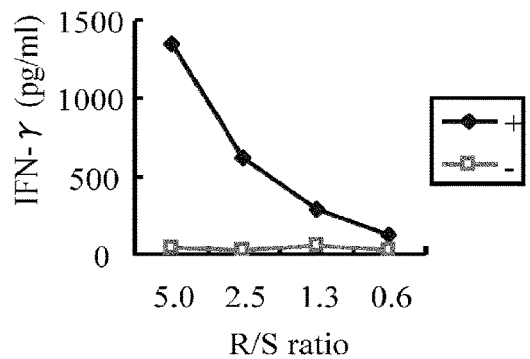
d  UBE2T-A02-10-102 #2
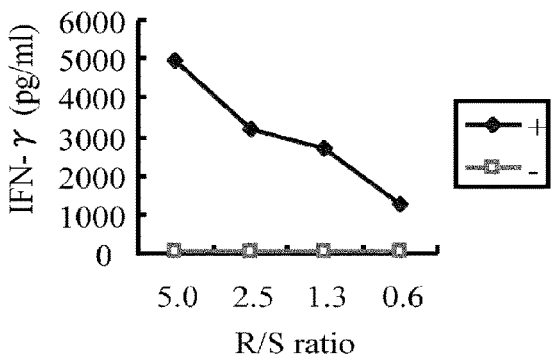
e  UBE2T-A02-10-101 #8

[Fig. 7]
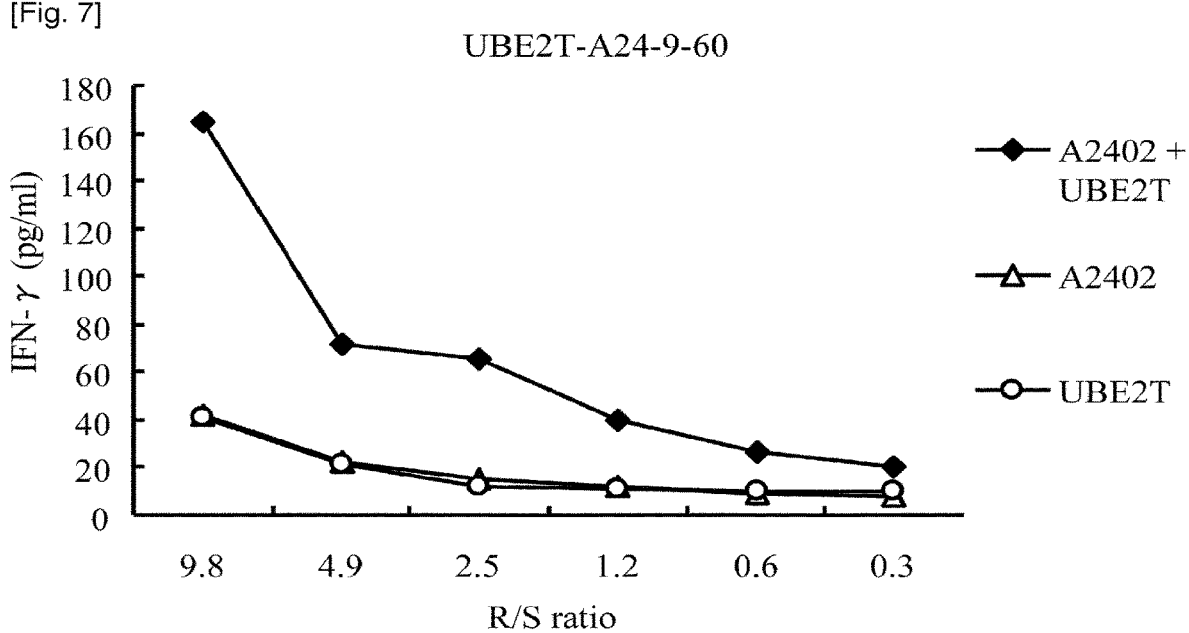
[Fig. 8]
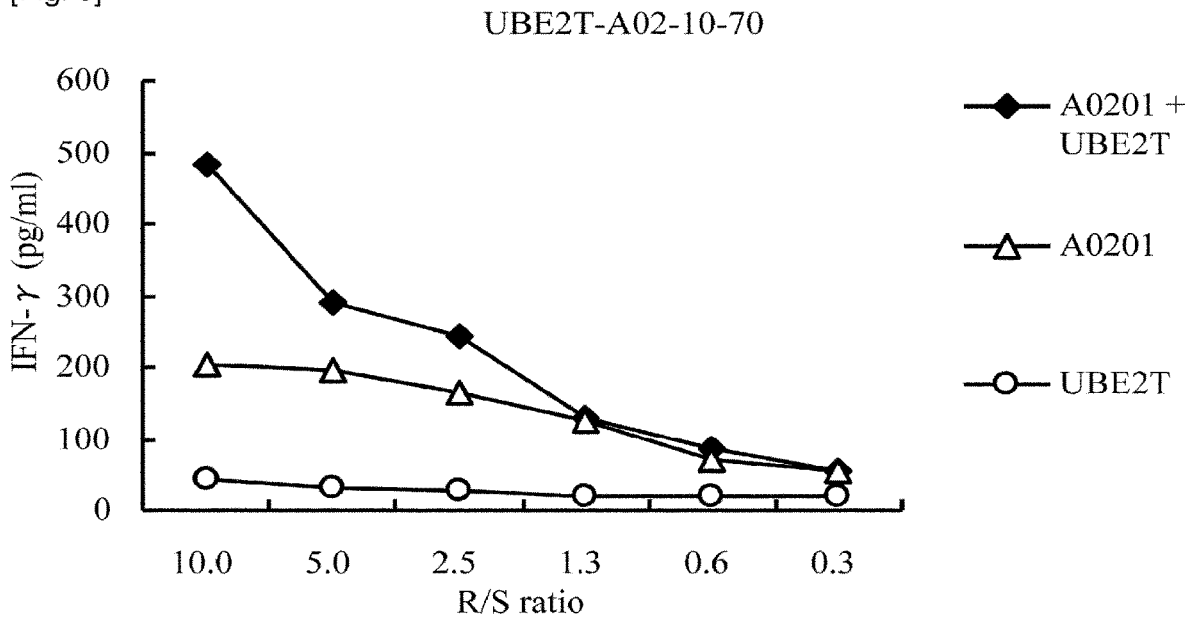

```
SEQUENCE LISTING

<160> NUMBER OF SEQ ID NOS: 69

<210> SEQ ID NO 1
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 1

Arg Tyr Pro Phe Glu Pro Pro Gln Ile
1               5

<210> SEQ ID NO 2
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 2

Pro Tyr Glu Lys Gly Val Phe Lys Leu
1               5

<210> SEQ ID NO 3
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 3

Leu Met Ala Asp Ile Ser Ser Glu Phe
1               5

<210> SEQ ID NO 4
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 4
```

```
Lys Tyr Asn Lys Pro Ala Phe Leu Lys
1               5
```

<210> SEQ ID NO 5
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 5

```
Val Ile Ile Pro Glu Arg Tyr Pro Phe
1               5
```

<210> SEQ ID NO 6
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 6

```
Ala Phe Leu Lys Asn Ala Arg Gln Trp
1               5
```

<210> SEQ ID NO 7
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 7

```
Arg Leu Lys Arg Glu Leu His Met Leu
1               5
```

<210> SEQ ID NO 8
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 8

```
Leu Thr Pro Ile Tyr His Pro Asn Ile
1               5
```

<210> SEQ ID NO 9
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 9

```
Glu Phe Lys Tyr Asn Lys Pro Ala Phe
1               5
```

<210> SEQ ID NO 10
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 10

```
Pro Phe Glu Pro Pro Gln Ile Arg Phe
1               5

<210> SEQ ID NO 11
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 11

Asn Thr Pro Tyr Glu Lys Gly Val Phe
1               5

<210> SEQ ID NO 12
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 12

Thr Val Leu Thr Ser Ile Gln Leu Leu
1               5

<210> SEQ ID NO 13
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 13

Arg Ala Ser Arg Leu Lys Arg Glu Leu
1               5

<210> SEQ ID NO 14
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 14

Arg Ile Cys Leu Asp Val Leu Lys Leu
1               5

<210> SEQ ID NO 15
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 15

Ala Thr Val Leu Thr Ser Ile Gln Leu
1               5

<210> SEQ ID NO 16
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 16

Ile Tyr His Pro Asn Ile Asp Ser Ala
```

<210> SEQ ID NO 17
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 17

Ser Glu Phe Lys Tyr Asn Lys Pro Ala Phe
1               5                   10

<210> SEQ ID NO 18
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 18

Pro Leu Met Ala Asp Ile Ser Ser Glu Phe
1               5                   10

<210> SEQ ID NO 19
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 19

Glu Phe Lys Tyr Asn Lys Pro Ala Phe Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 20

Lys Tyr Asn Lys Pro Ala Phe Leu Lys Asn
1               5                   10

<210> SEQ ID NO 21
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 21

Arg Pro Ser Leu Asn Ile Ala Thr Val Leu
1               5                   10

<210> SEQ ID NO 22
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 22

Lys Gln Lys Ala Asp Glu Glu Glu Met Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 23

Ala Thr Val Leu Thr Ser Ile Gln Leu Leu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 24

Met Ser Glu Pro Asn Pro Asp Asp Pro Leu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 25

Ser Thr Gln Lys Arg Lys Ala Ser Gln Leu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 26

Gln Met Asp Asp Leu Arg Ala Gln Ile Leu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 27

Thr Pro Tyr Glu Lys Gly Val Phe Lys Leu
1               5                   10

<210> SEQ ID NO 28
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 28

Glu Met Leu Asp Asn Leu Pro Glu Ala
1               5

```
<210> SEQ ID NO 29
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 29

Val Leu Thr Ser Ile Gln Leu Leu Met
1               5

<210> SEQ ID NO 30
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 30

Gln Met Asp Asp Leu Arg Ala Gln Ile
1               5

<210> SEQ ID NO 31
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 31

Asn Ile Ala Thr Val Leu Thr Ser Ile
1               5

<210> SEQ ID NO 32
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 32

Thr Val Leu Thr Ser Ile Gln Leu Leu
1               5

<210> SEQ ID NO 33
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 33

Leu Met Ala Asp Ile Ser Ser Glu Phe
1               5

<210> SEQ ID NO 34
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 34

Arg Leu Lys Arg Glu Leu His Met Leu
1               5
```

```
<210> SEQ ID NO 35
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 35

Ser Leu Asn Ile Ala Thr Val Leu Thr
1               5

<210> SEQ ID NO 36
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 36

Gly Val Phe Lys Leu Glu Val Ile Ile
1               5

<210> SEQ ID NO 37
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 37

Phe Leu Thr Pro Ile Tyr His Pro Asn
1               5

<210> SEQ ID NO 38
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 38

Met Leu Ala Thr Glu Pro Pro Pro Gly
1               5

<210> SEQ ID NO 39
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 39

Arg Ile Cys Leu Asp Val Leu Lys Leu
1               5

<210> SEQ ID NO 40
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 40

Pro Gln Ile Arg Phe Leu Thr Pro Ile
1               5

<210> SEQ ID NO 41
```

```
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 41

Phe Lys Tyr Asn Lys Pro Ala Phe Leu
 1               5

<210> SEQ ID NO 42
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 42

Gly Ala Trp Arg Pro Ser Leu Asn Ile
 1               5

<210> SEQ ID NO 43
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 43

Ser Ala Gly Arg Ile Cys Leu Asp Val
 1               5

<210> SEQ ID NO 44
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 44

Leu Ala Thr Glu Pro Pro Pro Gly Ile
 1               5

<210> SEQ ID NO 45
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 45

Ala Thr Val Leu Thr Ser Ile Gln Leu
 1               5

<210> SEQ ID NO 46
<211> LENGTH: 9
<212> TYPE: PRT
<213> ORGANISM: Artificial Sequence
<220> FEATURE:
<223> OTHER INFORMATION: a peptide derived from UBE2T

<400> SEQUENCE: 46

Phe Leu Lys Asn Ala Arg Gln Trp Thr
 1               5

<210> SEQ ID NO 47
<211> LENGTH: 10
```

<212> TYPE: PRT
<213> ORGANISM: Artificial Sequence
<220> FEATURE:
<223> OTHER INFORMATION: a peptide derived from UBE2T

<400> SEQUENCE: 47

Met Leu Ala Thr Glu Pro Pro Pro Gly Ile
1               5                   10

<210> SEQ ID NO 48
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 48

Phe Leu Thr Pro Ile Tyr His Pro Asn Ile
1               5                   10

<210> SEQ ID NO 49
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 49

Arg Leu Lys Arg Glu Leu His Met Leu Ala
1               5                   10

<210> SEQ ID NO 50
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 50

Asn Leu Pro Glu Ala Gly Asp Ser Arg Val
1               5                   10

<210> SEQ ID NO 51
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 51

Thr Val Leu Thr Ser Ile Gln Leu Leu Met
1               5                   10

<210> SEQ ID NO 52
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 52

Leu Asn Ile Ala Thr Val Leu Thr Ser Ile
1               5                   10

<210> SEQ ID NO 53
<211> LENGTH: 10
<212> TYPE: PRT

```
<213> ORGANISM: Artificial Sequence
<220> FEATURE:
<223> OTHER INFORMATION: a peptide derived from UBE2T

<400> SEQUENCE: 53

Gln Met Asp Asp Leu Arg Ala Gln Ile Leu
1               5                   10

<210> SEQ ID NO 54
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 54

His Met Leu Ala Thr Glu Pro Pro Pro Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 55

Ser Leu Asn Ile Ala Thr Val Leu Thr Ser
1               5                   10

<210> SEQ ID NO 56
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 56

Asp Gln Met Asp Asp Leu Arg Ala Gln Ile
1               5                   10

<210> SEQ ID NO 57
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 57

Ala Thr Val Leu Thr Ser Ile Gln Leu Leu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 58

Ile Leu Gly Gly Ala Asn Thr Pro Tyr Glu
1               5                   10

<210> SEQ ID NO 59
<211> LENGTH: 10
<212> TYPE: PRT
<213> ORGANISM: Artificial Sequence
```

```
<220> FEATURE:
<223> OTHER INFORMATION: a peptide derived from UBE2T

<400> SEQUENCE: 59

Val Leu Thr Ser Ile Gln Leu Leu Met Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 60

Glu Met Leu Asp Asn Leu Pro Glu Ala Gly
1               5                   10

<210> SEQ ID NO 61
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 61

Leu Leu Met Ser Glu Pro Asn Pro Asp Asp
1               5                   10

<210> SEQ ID NO 62
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 62

Ile Ala Thr Val Leu Thr Ser Ile Gln Leu
1               5                   10

<210> SEQ ID NO 63
<211> LENGTH: 10
<212> TYPE: PRT
<213> ORGANISM: Artificial Sequence
<220> FEATURE:
<223> OTHER INFORMATION: a peptide derived from UBE2T

<400> SEQUENCE: 63

Thr Pro Tyr Glu Lys Gly Val Phe Lys Leu
1               5                   10

<210> SEQ ID NO 64
<211> LENGTH: 935
<212> TYPE: DNA
<213> ORGANISM: Homo sapiens
<220> FEATURE:
<221> NAME/KEY: CDS
<222> LOCATION: (137)..(730)

<400> SEQUENCE: 64
agtcagaggt cgcgcaggcg ctggtacccc gttggtccgc gcgttgctgc gttgtgaggg     60
gtgtcagctc agtgcatccc aggcagctct tagtgtggag cagtgaactg tgtgtggttc    120
cttctacttg gggatc atg cag aga gct tca cgt ctg aag aga gag ctg cac    172
                Met Gln Arg Ala Ser Arg Leu Lys Arg Glu Leu His
                1               5                   10
```

| | | |
|---|---|---|
| atg tta gcc aca gag cca ccc cca ggc atc aca tgt tgg caa gat aaa<br>Met Leu Ala Thr Glu Pro Pro Pro Gly Ile Thr Cys Trp Gln Asp Lys<br>               15                      20                   25 | 220 | |
| gac caa atg gat gac ctg cga gct caa ata tta ggt gga gcc aac aca<br>Asp Gln Met Asp Asp Leu Arg Ala Gln Ile Leu Gly Gly Ala Asn Thr<br> 30                         35                      40 | 268 | |
| cct tat gag aaa ggt gtt ttt aag cta gaa gtt atc att cct gag agg<br>Pro Tyr Glu Lys Gly Val Phe Lys Leu Glu Val Ile Ile Pro Glu Arg<br> 45                         50                      55                      60 | 316 | |
| tac cca ttt gaa cct cct cag atc cga ttt ctc act cca att tat cat<br>Tyr Pro Phe Glu Pro Pro Gln Ile Arg Phe Leu Thr Pro Ile Tyr His<br>                         65                              70                         75 | 364 | |
| cca aac att gat tct gct gga agg att tgt ctg gat gtt ctc aaa ttg<br>Pro Asn Ile Asp Ser Ala Gly Arg Ile Cys Leu Asp Val Leu Lys Leu<br>                   80                           85                      90 | 412 | |
| cca cca aaa ggt gct tgg aga cca tcc ctc aac atc gca act gtg ttg<br>Pro Pro Lys Gly Ala Trp Arg Pro Ser Leu Asn Ile Ala Thr Val Leu<br>                95                     100                     105 | 460 | |
| acc tct att cag ctg ctc atg tca gaa ccc aac cct gat gac ccg ctc<br>Thr Ser Ile Gln Leu Leu Met Ser Glu Pro Asn Pro Asp Asp Pro Leu<br>110                         115                     120 | 508 | |
| atg gct gac ata tcc tca gaa ttt aaa tat aat aag cca gcc ttc ctc<br>Met Ala Asp Ile Ser Ser Glu Phe Lys Tyr Asn Lys Pro Ala Phe Leu<br>125                         130                     135                     140 | 556 | |
| aag aat gcc aga cag tgg aca gag aag cat gca aga cag aaa caa aag<br>Lys Asn Ala Arg Gln Trp Thr Glu Lys His Ala Arg Gln Lys Gln Lys<br>                   145                     150                     155 | 604 | |
| gct gat gag gaa gag atg ctt gat aat cta cca gag gct ggt gac tcc<br>Ala Asp Glu Glu Glu Met Leu Asp Asn Leu Pro Glu Ala Gly Asp Ser<br>                160                     165                     170 | 652 | |
| aga gta cac aac tca aca cag aaa agg aag gcc agt cag cta gta ggc<br>Arg Val His Asn Ser Thr Gln Lys Arg Lys Ala Ser Gln Leu Val Gly<br>                   175                     180                     185 | 700 | |
| ata gaa aag aaa ttt cat cct gat gtt tag gggacttgtc ctggttcatc<br>Ile Glu Lys Lys Phe His Pro Asp Val<br>        190                     195 | 750 | |
| ttagttaatg tgttctttgc caaggtgatc taagttgcct accttgaatt tttttttaaa | 810 | |
| tatatttgat gacataattt ttgtgtagtt tatttatctt gtacatatgt attttgaaat | 870 | |
| cttttaaacc tgaaaataa atagtcattt aatgttgaaa aaaaaaaaa aaaaaaaaa | 930 | |
| aaaaa | 935 | |

<210> SEQ ID NO 65
<211> LENGTH: 197
<212> TYPE: PRT
<213> ORGANISM: Homo sapiens

<400> SEQUENCE: 65

Met Gln Arg Ala Ser Arg Leu Lys Arg Glu Leu His Met Leu Ala Thr
1                  5                     10                    15

Glu Pro Pro Pro Gly Ile Thr Cys Trp Gln Asp Lys Asp Gln Met Asp
                   20                     25                    30

Asp Leu Arg Ala Gln Ile Leu Gly Gly Ala Asn Thr Pro Tyr Glu Lys
              35                     40                    45

Gly Val Phe Lys Leu Glu Val Ile Ile Pro Glu Arg Tyr Pro Phe Glu
    50                     55                     60

Pro Pro Gln Ile Arg Phe Leu Thr Pro Ile Tyr His Pro Asn Ile Asp
65                  70                     75                    80

```
Ser Ala Gly Arg Ile Cys Leu Asp Val Leu Lys Leu Pro Pro Lys Gly
            85                  90                  95

Ala Trp Arg Pro Ser Leu Asn Ile Ala Thr Val Leu Thr Ser Ile Gln
        100                 105                 110

Leu Leu Met Ser Glu Pro Asn Pro Asp Pro Leu Met Ala Asp Ile
        115                 120                 125

Ser Ser Glu Phe Lys Tyr Asn Lys Pro Ala Phe Leu Lys Asn Ala Arg
    130                 135                 140

Gln Trp Thr Glu Lys His Ala Arg Gln Lys Gln Lys Ala Asp Glu Glu
145                 150                 155                 160

Glu Met Leu Asp Asn Leu Pro Glu Ala Gly Asp Ser Arg Val His Asn
            165                 170                 175

Ser Thr Gln Lys Arg Lys Ala Ser Gln Leu Val Gly Ile Glu Lys Lys
        180                 185                 190

Phe His Pro Asp Val
        195

<210> SEQ ID NO 66
<211> LENGTH: 22
<212> TYPE: DNA
<213> ORGANISM: Artificial Sequence
<220> FEATURE:
<223> OTHER INFORMATION: a PCR primer for the TCR analysis

<400> SEQUENCE: 66
gtctaccagg cattcgcttc at                                          22

<210> SEQ ID NO 67
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 67
tcagctggac cacagccgca gcgt                                        24

<210> SEQ ID NO 68
<211> LENGTH: 21
<212> TYPE: DNA
<213> ORGANISM: Artificial Sequence
<220> FEATURE:
<223> OTHER INFORMATION: a PCR primer for the TCR analysis

<400> SEQUENCE: 68
tcagaaatcc tttctcttga c                                           21

<210> SEQ ID NO 69
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 69
ctagcctctg gaatcctttc tctt                                        24
```

UBE2T PEPTIDES AND VACCINES CONTAINING THE SAME

CROSS-REFERENCE TO RELATED APPLICATIONS

The present application is a Divisional of U.S. patent application Ser. No. 14/400,169, filed Nov. 10, 2014 which is a National Stage of International Application No. PCT/JP2013/005321, filed Sep. 9, 2013, and which claims the benefit of U.S. Provisional Application No. 61/699,550, filed on Sep. 11, 2012, the entire contents of which are incorporated by reference herein.

TECHNICAL FIELD

The present invention relates to the field of biological science, more specifically to the field of cancer therapy. In particular, the present invention relates to novel peptides that are effective as cancer vaccines, as well as drugs for either or both of treating and preventing tumors.

REFERENCE TO SEQUENCE LISTING

This application includes a Sequence Listing as a text file named "087331-1100418 SEQLIST.txt" created Aug. 13, 2018, and containing 20,000 bytes. The material contained in this text file is incorporated by reference in its entirety for all purposes.

BACKGROUND ART

It has been demonstrated that CD8 positive cytotoxic T lymphocytes (CTLs) recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1-2). Some of these TAAs are currently undergoing clinical development as immunotherapeutic targets.

Favorable TAAs are indispensable for the proliferation and survival of cancer cells. The use of such TAAs as targets for immunotherapy may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses warrants further development and thus clinical application of peptide vaccination strategies for various types of cancer in ongoing (NPL 3-10). To date, there have been several reports of clinical trials using these TAAs-derived peptides. Unfortunately, only a low objective response rate has been observed in these cancer vaccine trials (NPL 11-13). Accordingly, there remains a need for new TAAs as immunotherapeutic targets.

UBE2T (ubiquitin-conjugating enzyme E2T: a typical amino acid sequence shown in SEQ ID NO: 65; a typical nucleotide sequence shown in SEQ ID NO: 64 (GenBank Accession No. NM_014176)) is one of the ubiquitin-conjugating enzymes (E2). UBE2T was reported to be one of the genes whose expression was up-regulated in human fibroblasts with serum stimulation (NPL 14). In the Fanconi anemia pathway, UBE2T binds FANCL, and is necessary for the DNA damage-induced monoubiquitination of FANCD2 (NPL 15-16). In recent studies, UBE2T was found to be frequently up-regulated in breast cancers, and interact and co-localize with the BRCA1/BRCA1-associated RING domain protein (BARD1) complex (PTL 1, NPL 17). Northern blot analysis in those studies revealed that UBE2T transcript was detected at very high level in breast cancer cell lines, but hardly detected in the vital organs. Furthermore, knockdowns of endogenous UBE2T by siRNA in cancer cell lines have been shown to significantly suppress growth of those cell lines (PTL 1-2, NPL 17).

CITATION LIST

Patent Literature

[PTL 1] WO2005/029067
[PTL 2] WO2009/001562

Non Patent Literature

[NPL 1] Boon T, Int J Cancer 1993, 54(2): 177-80
[NPL 2] Boon T & van der Bruggen P, J Exp Med 1996, 183(3): 725-9
[NPL 3] Harris C C, J Natl Cancer Inst 1996, 88(20): 1442-55
[NPL 4] Butterfield L H et al., Cancer Res 1999, 59(13): 3134-42
[NPL 5] Vissers J L et al., Cancer Res 1999, 59(21): 5554-9
[NPL 6] van der Burg S H et al., J Immunol 1996, 156(9): 3308-14
[NPL 7] Tanaka F et al., Cancer Res 1997, 57(20): 4465-8
[NPL 8] Fujie T et al., Int J Cancer 1999, 80(2): 169-72
[NPL 9] Kikuchi M et al., Int J Cancer 1999, 81(3): 459-66
[NPL 10] Oiso M et al., Int J Cancer 1999, 81(3): 387-94
[NPL 11] Belli F et al., J Clin Oncol 2002, 20(20): 4169-80
[NPL 12] Coulie P G et al., Immunol Rev 2002, 188: 33-42
[NPL 13] Rosenberg S A et al., Nat Med 2004, 10(9): 909-15
[NPL 14] Iyer V R et al., Science 1999, 283: 83-7
[NPL 15] Machida Y J et al., Mol Cell 2006, 23: 589-96
[NPL 16] Alpi A et al., Mol Cell Biol 2007, 27: 8421-30
[NPL 17] Ueki T et. al., Cancer Res. 2009, 69: 8752-60

SUMMARY OF INVENTION

The present invention is based, at least in part, on the discovery of novel peptides that may serve as suitable targets of immunotherapy. Because TAAs are generally perceived by the immune system as "self" and therefore often have no innate immunogenicity, the discovery of appropriate targets is still of importance.

To that end, the present invention is directed, at least in part, to the identification of specific epitope peptides that possess the ability to induce CTLs specific to UBE2T among peptides derived from UBE2T.

The results disclosed herein demonstrate that identified peptides are HLA-A24 or HLA-A2 restricted epitope peptides that can induce potent and specific immune responses against cells expressing UBE2T.

Accordingly, it is an object of the present invention to provide UBE2T-derived peptides that can be used to induce CTLs in vitro, ex vivo or in vivo, or to be administered to a subject for inducing immune responses against cancers, examples of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor. Preferred peptides are nonapeptides and decapeptides, more preferably nonapeptides and decapeptides having an amino acid sequence selected from among SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58. Of these, the peptides having an amino acid sequence selected from among SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58 are particularly preferred.

The present invention also contemplates modified peptides having an amino acid sequence selected from among SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58 in which one, two or more amino acids are substituted, deleted, inserted and/or added, as long as the resulting modified peptides retain the requisite CTL inducibility of the original unmodified peptide. In one embodiment, when the original peptides is 9 mer (SEQ ID NOs: 1, 2, 4, 6, 11, 12, 13, 15, 29, 30, 32, 36, 38, and 41), the size of the modified peptide is preferably in the range of 9 to 40 amino acids, such as in the range of 9 to 20 amino acids, for example in the range 9 to 15 amino acids. Likewise, when the original peptides is 10 mer (SEQ ID NOs: 17, 19, 20, 21, 22, 23, 24, 25, 27, 48, 49, 51, 52, 53, 55, 56 and 58), the size of the modified peptide is preferably in the range of 10 to 40 amino acids, such as in the range of 10 to 20 amino acids, for example in the range 10 to 15 amino acids.

The present invention further encompasses isolated polynucleotides encoding any one of the peptides of the present invention. These polynucleotides can be used to induce or prepare antigen-presenting cells (APCs) having CTL inducibility. Like the peptides of the present invention, such APCs can be administered to a subject for inducing immune responses against cancers.

When administered to a subject, the peptides of the present invention can be presented on the surface of APCs so as to induce CTLs targeting the respective peptides. Therefore, one object of the present invention is to provide agents or compositions including one or more peptides of the present invention, or polynucleotides encoding such peptides. The agent or composition may be used for inducing a CTL. Such agents or compositions can be used for the treatment and/or prophylaxis of a cancer, and/or the prevention of a metastasis or post-operative recurrence thereof. Examples of cancers contemplated by the present invention include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

The present invention further contemplates pharmaceutical compositions or agents that include one or more peptides or polynucleotides of the present invention. The pharmaceutical composition is preferably formulated for use in the treatment and/or prophylaxis of a cancer, and/or prevention of metastasis or postoperative recurrence thereof. Instead of or in addition to the peptides or polynucleotides of the present invention, the pharmaceutical agents or compositions of the present invention may include as active ingredients APCs and/or exosomes that present any of the peptides of the present invention.

The peptides or polynucleotides of the present invention may be used to induce APCs that present on the surface a complex of a human leukocyte antigen (HLA) and a peptide of the present invention, for example, by contacting APCs derived from a subject with the peptide of the present invention or introducing a polynucleotide encoding the peptide of the present invention into APCs. Such APCs have the ability to induce CTLs that specifically recognize cells that present target peptides on the surface and are useful for cancer immunotherapy. Accordingly, the present invention encompasses the methods for inducing APCs with CTL inducibility as well as the APCs obtained by such methods.

In addition, the present invention also encompasses the agents or compositions for inducing APCs having CTL inducibility, such agents or compositions including any peptides or polynucleotides of the present invention.

It is a further object of the present invention to provide methods for inducing CTLs, such methods including the step of co-culturing CD8 positive T cells with APCs presenting on its surface a complex of an HLA antigen and the peptide of the present invention, the step of co-culturing CD8 positive T cells with exosomes presenting on its surface a complex of an HLA antigen and the peptide of the present invention, or the step of introducing a polynucleotide encoding both of T cell receptor (TCR) subunits or polynucleotides encoding each of TCR subunits, wherein the TCR can bind to a complex of the peptide of the present invention and an HLA antigen presented on cell surface. CTLs obtained by such methods can find use in the treatment and/or prevention of cancers, examples of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor. Therefore, the present invention also encompasses CTLs obtained by above-described methods.

Yet another object of the present invention is to provide isolated APCs that present on the surface a complex of an HLA antigen and a peptide of the present invention. The present invention further provides isolated CTLs that target peptides of the present invention. Such CTLs may be also defined as CTLs that can recognize (or bind to) a complex of a peptide of the present invention and an HLA antigen on the cell surface. These APCs and CTLs may be used for cancer immunotherapy.

It is yet another object of the present invention to provide methods for inducing an immune response against a cancer in a subject in need thereof, such methods including the step of administering to the subject an agent or composition including at least one component selected from among a peptide of the present invention or a polynucleotide encoding thereof, an APC or exosome presenting thereof and a CTL that can recognize a cell presenting the peptide of the present invention on the surface.

One aspect of the present invention pertains to a peptide of the present invention or a composition comprising a peptide of the present invention for use a medicament.

The applicability of the present invention extends to any of a number of diseases relating to or arising from UBE2T overexpression, such as cancer, examples of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

More specifically, the present invention provides followings:

[1] An isolated peptide having cytotoxic T lymphocyte (CTL) inducibility, wherein the peptide comprises an amino acid sequence (a) or (b) below:
(a) an amino acid sequence of an immunologically active fragment of UBE2T;
(b) an amino acid sequence in which 1, 2, or several amino acid(s) are substituted, deleted, inserted and/or added in an amino acid sequence of an immunologically active fragment of UBE2T,
wherein the CTL induced by the peptide has specific cytotoxic activity against a cell that presents a fragment derived from UBE2T;

[2] The peptide of [1], wherein the peptide comprises an amino acid sequence (a) or (b) below:
(a) an amino acid sequence selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58;
(b) an amino acid sequence in which 1, 2, or several amino acid(s) are substituted, deleted, inserted and/or added in the amino acid sequence selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58; The size of the modified peptide is preferably in the range of 9 to 40 amino acids, such as in the range of 9 to 20 amino acids, for example in the range 9 to 15 amino acids;

[3] The peptide of [2], wherein the peptide is the following oligopeptide (i) or (ii):
(i) a peptide that has one or both of the following characteristics:
(a) the second amino acid from the N-terminus of the amino acid sequence of SEQ ID NO: 1, 2, 4, 6, 11, 12, 13, 15, 17, 19, 20, 21, 22, 23, 24, 25 or 27 is substituted with phenylalanine, tyrosine, methionine or tryptophan; and
(b) the C-terminal amino acid of the amino acid sequence of SEQ ID NO: 1, 2, 4, 6, 11, 12, 13, 15, 17, 19, 20, 21, 22, 23, 24, 25 or 27 is substituted with phenylalanine, leucine, isoleucine, tryptophan or methionine;
(ii) a peptide that has one or both of the following characteristics:
(a) the second amino acid from the N-terminus of the amino acid sequence of SEQ ID NO: 29, 30, 32, 36, 38, 41, 48, 49, 51, 52, 53, 55, 56 or 58 is substituted with leucine or methionine; and
(b) the C-terminal amino acid of the amino acid sequence of SEQ ID NO: 29, 30, 32, 36, 38, 41, 48, 49, 51, 52, 53, 55, 56 or 58 is substituted with valine or leucine;

[4] The peptide of any one of [1] to [3], wherein the peptide is a nonapeptide or a decapeptide;

[5] The peptide of [4], wherein the peptide consists of the amino acid sequence selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58;

[6] An isolated polynucleotide encoding the peptide of any one of [1] to [5];

[7] A composition for inducing a CTL, wherein the composition comprises at least one active ingredient selected from the group consisting of:
(a) the peptide of any one of [1] to [5];
(b) the polynucleotide of [6];
(c) an APC that presents the peptide of any one of [1] to [5] on its surface; and
(d) an exosome that presents the peptide of any one of [1] to [5] on its surface;

[8] A pharmaceutical composition for the treatment and/or prophylaxis of cancer, and/or the prevention of a postoperative recurrence thereof, wherein the composition comprises at least one active ingredient selected from the group consisting of:
(a) the peptide of any one of [1] to [5];
(b) the polynucleotide of [6];
(c) an APC that presents the peptide of any one of [1] to [5] on its surface;
(d) an exosome that presents the peptide of any one of [1] to [5] on its surface; and
(e) a CTL that can recognize a cell presenting the peptide of any one of [1] to [5];

[9] The pharmaceutical composition of [8], wherein the pharmaceutical composition is formulated for the administration to a subject whose HLA antigen is HLA-A24 or HLA-A2;

[10] A method for inducing an APC with CTL inducibility, wherein the method comprises the step selected from the group consisting of:
(a) contacting an APC with the peptide of any one of [1] to [5], and
(b) introducing a polynucleotide encoding the peptide of any one of [1] to [5] into an APC;

[11] A method for inducing a CTL, wherein the method comprises a step selected from the group consisting of:
(a) co-culturing a CD8 positive T cell with an APC that presents on its surface a complex of an HLA antigen and the peptide of any one of [1] to [5];
(b) co-culturing a CD8 positive T cell with an exosome that presents on its surface a complex of an HLA antigen and the peptide of any one of [1] to [5]; and
(c) introducing into a CD8 positive T cell a polynucleotide encoding both of TCR subunits or polynucleotides encoding each of TCR subunits, wherein the TCR formed by said subunits can bind to a complex of the peptide of any one of [1] to [5] and an HLA antigen on a cell surface;

[12] An isolated APC that presents on its surface a complex of an HLA antigen and the peptide of any one of [1] to [5];

[13] The APC of [12], which is induced by the method of [10];

[14] An isolated CTL that targets the peptide of any one of [1] to [5];

[15] The CTL of [14], which is induced by the method of [11];

[16] A method of inducing an immune response against cancer in a subject, wherein the method comprises the step of administering to the subject a composition comprising the peptide of any one of [1] to [5], or a polynucleotide encoding the peptide;

[17] An antibody or immunologically active fragment thereof against the peptide of any one of [1] to [5];

[18] A vector comprising a nucleotide sequence encoding the peptide of any one of [1] to [5];
Preferably the vector is adapted for expression of said peptide (referred to as expression vector), e.g. the encoding nucleotide sequence is inserted in vector downstream of a promoter sequence and operably linked to said promoter sequence. The term "operably linked" is intended to mean that the nucleotide sequence is linked to the promoter sequence (regulatory sequence) such that it allows expression of the nucleotide sequence in vitro or in a host cell in which the vector is introduced;

[19] A host cell transformed or transfected with a vector of [18] or expression vector described herein;

[20] A diagnostic kit comprising the peptide of any one of [1] to [5], the polynucleotide of [6] or the antibody or immunologically active fragment of [17]; and

[21] A method of screening for a peptide having an ability to induce a CTL that has wherein the method comprises the steps of:
(i) providing a candidate sequence consisting of an amino acid sequence modified by substituting, deleting, inserting and/or adding one, two or several amino acid residues to an original amino acid sequence, wherein the original amino acid sequence is selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58;
(ii) selecting a candidate sequence that does not have substantial significant homology (or sequence identity) with the peptides derived from any known human gene products other than UBE2T;
(iii) contacting a peptide consisting of the candidate sequence selected in step (ii) with an antigen presenting cell;
(iv) contacting the antigen presenting cell of step (iii) with a CD8 positive T cell; and
(v) identifying the peptide of which CTL inducibility is same to or higher than a peptide consisting of the original amino acid sequence.

[22] A pharmaceutical composition comprising peptide of any one of [1] to [5].

[23] A peptide of any one of [1] to [5] for use as a medicament.

[24] A polynucleotide of [6] or a vector of [18] for use as a medicament.

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention.

In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments that follows.

FIG. 1a-1 is composed of a series of photographs, (a) to (l), showing the results of interferon (IFN)-gamma enzyme-linked immunospot (ELISPOT) assay on CTLs that were induced with peptides derived from UBE2T. The CTLs in the well number #8 stimulated with UBE2T-A24-9-60 (SEQ ID NO: 1) (a), #1 stimulated with UBE2T-A24-9-45 (SEQ ID NO: 2) (b), #6 stimulated with UBE2T-A24-9-133 (SEQ ID NO: 4) (c), #6 stimulated with UBE2T-A24-9-138 (SEQ ID NO: 6) (d), #4 stimulated with UBE2T-A24-9-43 (SEQ ID NO: 11) (e), #2 stimulated with UBE2T-A24-9-106 (SEQ ID NO: 12) (f), #6 stimulated with UBE2T-A24-9-3 (SEQ ID NO: 13) (g), #3 stimulated with UBE2T-A24-9-105 (SEQ ID NO: 15) (h), #2 stimulated with UBE2T-A24-10-130 (SEQ ID NO: 17) (i), #1 stimulated with UBE2T-A24-10-131 (SEQ ID NO: 19) (j), #3 stimulated with UBE2T-A24-10-133 (SEQ ID NO: 20) (k), and #6 stimulated with UBE2T-A24-10-99 (SEQ ID NO: 21) (l) showed potent IFN-gamma production compared with the control, respectively. The square on the well of these pictures indicates that the cells from corresponding well were expanded to establish CTL lines. In contrast, as a typical case of a negative data, specific IFN-gamma production from the CTL stimulated with UBE2T-A24-9-124 (SEQ ID NO: 3) (r) was not shown. In the figures, "+" indicates the IFN-gamma production against target cells pulsed with the appropriate peptide, and "−" indicates the IFN-gamma production against target cells not pulsed with any peptides.

FIG. 1m-r is composed of a series of photographs, (m) to (r), showing the results of interferon (IFN)-gamma enzyme-linked immunospot (ELISPOT) assay on CTLs that were induced with peptides derived from UBE2T. The CTLs in the well number #7 stimulated with UBE2T-A24-10-154 (SEQ ID NO: 22) (m), #8 stimulated with UBE2T-A24-10-105 (SEQ ID NO: 23) (n), #1 stimulated with UBE2T-A24-10-115 (SEQ ID NO: 24) (o), #4 stimulated with UBE2T-A24-10-177 (SEQ ID NO: 25) (p) and #7 stimulated with UBE2T-A24-10-44 (SEQ ID NO: 27) (q) showed potent IFN-gamma production compared with the control, respectively. The square on the well of these pictures indicates that the cells from corresponding well were expanded to establish CTL lines. In contrast, as a typical case of a negative data, specific IFN-gamma production from the CTL stimulated with UBE2T-A24-9-124 (SEQ ID NO: 3) (r) was not shown. In the figures, "+" indicates the IFN-gamma production against target cells pulsed with the appropriate peptide, and "−" indicates the IFN-gamma production against target cells not pulsed with any peptides.

FIG. 2a-l is composed of a series of photographs, (a) to (l), showing the results of ELISPOT assay on CTLs that were induced with peptides derived from UBE2T. The CTLs in the well number #4 stimulated with UBE2T-A02-9-107 (SEQ ID NO: 29) (a), #5 stimulated with UBE2T-A02-9-30 (SEQ ID NO: 30) (b), #7 stimulated with UBE2T-A02-9-106 (SEQ ID NO: 32) (c), #5 stimulated with UBE2T-A02-9-49 (SEQ ID NO: 36) (d), #3 stimulated with UBE2T-A02-9-13 (SEQ ID NO: 38) (e), #4 stimulated with UBE2T-A02-9-132 (SEQ ID NO: 41) (f), #6 stimulated with UBE2T-A02-10-70 (SEQ ID NO: 48) (g), #7 stimulated with UBE2T-A02-10-6 (SEQ ID NO: 49) (h), #8 stimulated with UBE2T-A02-10-106 (SEQ ID NO: 51) (i), #2 stimulated with UBE2T-A02-10-102 (SEQ ID NO: 52) (j), #1 stimulated with UBE2T-A02-10-30 (SEQ ID NO: 53) (k), and #8 stimulated with UBE2T-A02-10-101 (SEQ ID NO: 55) (l) showed potent IFN-gamma production compared with the control, respectively. The square on the well of these pictures indicates that the cells from corresponding well were expanded to establish CTL lines. In contrast, as a typical case of a negative data, specific IFN-gamma production from the CTL stimulated with UBE2T-A02-9-161 (SEQ ID NO: 28) (o) was not shown. In the figures, "+" indicates the IFN-gamma production against target cells pulsed with the appropriate peptide, and "−" indicates the IFN-gamma production against target cells not pulsed with any peptides.

FIG. 2m-o is composed of a series of photographs, (m) to (o), showing the results of ELISPOT assay on CTLs that were induced with peptides derived from UBE2T. The CTLs in the well number #5 stimulated with UBE2T-A02-10-29 (SEQ ID NO: 56) (m) and #3 stimulated with UBE2T-A02-10-38 (SEQ ID NO: 58) (n) showed potent IFN-gamma production compared with the control, respectively. The square on the well of these pictures indicates that the cells from corresponding well were expanded to establish CTL lines. In contrast, as a typical case of a negative data, specific IFN-gamma production from the CTL stimulated with UBE2T-A02-9-161 (SEQ ID NO: 28) (o) was not shown. In the figures, "+" indicates the IFN-gamma production against target cells pulsed with the appropriate peptide, and "−" indicates the IFN-gamma production against target cells not pulsed with any peptides.

FIG. 3 is composed of a series of line graphs, (a) to (d), showing the IFN-gamma production of the CTL lines stimulated with UBE2T-A24-9-60 (SEQ ID NO: 1) (a), UBE2T-A24-9-45 (SEQ ID NO: 2) (b), UBE2T-A24-9-3 (SEQ ID NO: 13) (c) and UBE2T-A24-10-44 (SEQ ID NO: 27) (d). The quantity of IFN-gamma which CTLs produced was measured by IFN-gamma enzyme-linked immunosorbent assay (ELISA). The results demonstrates that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.

FIG. 4 is composed of a series of line graphs, (a) to (c), showing the IFN-gamma production of the CTL clones established by limiting dilution from the CTL lines stimulated with UBE2T-A24-9-60 (SEQ ID NO: 1) (a), UBE2T-A24-9-45 (SEQ ID NO: 2) (b) and UBE2T-A24-9-3 (SEQ ID NO: 13) (c). The results demonstrate that the CTL clones established by stimulation with each peptide show potent IFN-gamma production as compared with the control. In the figures, "+" indicates the IFN-gamma production against target cells pulsed with the appropriate peptide and "−" indicates the IFN-gamma production against target cells not pulsed with any peptides. R/S ratio indicates the ratio of the number of responder cells (CTL clone) and stimulator cells.

FIG. 5 is composed of a series of line graphs, (a) to (e), showing the IFN-gamma production of the CTL lines stimulated with UBE2T-A02-9-107 (SEQ ID NO: 29) (a), UBE2T-A02-9-13 (SEQ ID NO: 38) (b), UBE2T-A02-10-70 (SEQ ID NO: 48) (c), UBE2T-A02-10-102 (SEQ ID NO: 52) (d) and UBE2T-A02-10-101 (SEQ ID NO: 55) (e). The quantity of IFN-gamma which CTL produced was measured by IFN-gamma ELISA. The results demonstrate that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides. R/S ratio indicates the ratio of the number of responder cells (CTL line) and stimulator cells.

FIG. 6 is composed of series of line graphs, (a) to (e), showing the IFN-gamma production of the CTL clones established by limiting dilution from the CTL lines stimulated with UBE2T-A02-9-107 (SEQ ID NO: 29) (a), UBE2T-A02-9-13 (SEQ ID NO: 38) (b), UBE2T-A02-10-70 (SEQ ID NO: 48) (c), UBE2T-A02-10-102 (SEQ ID NO: 52) (d) and UBE2T-A02-10-101 (SEQ ID NO: 55) (e). The results demonstrate that the CTL clones established by stimulation with each peptide show potent IFN-gamma production as compared with the control. In the figures, "+" indicates the IFN-gamma production against target cells pulsed with the appropriate peptide and "−" indicates the IFN-gamma production against target cells not pulsed with any peptides. R/S ratio indicates the ratio of the number of responder cells (CTL clone) and stimulator cells.

FIG. 7 is a line graph, showing specific CTL activity against the target cells that express UBE2T and HLA-A*2402. COS7 cells transfected with HLA-A*2402 or the full length of the UBE2T gene were prepared as controls. The CTL clone established with UBE2T-A24-9-60 (SEQ ID NO: 1) showed specific CTL activity against COS7 cells transfected with both UBE2T and HLA-A*2402 (black lozenge). On the other hand, no significant specific CTL activity was detected against target cells expressing either HLA-A*2402 (triangle) or UBE2T (circle).

FIG. 8 is a line graph, showing specific CTL activity against the target cells that express UBE2T and HLA-A*0201. COS7 cells transfected with HLA-A*0201 or the full length of the UBE2T gene were prepared as controls. The CTL line established with UBE2T-A02-10-70 (SEQ ID NO: 48) showed specific CTL activity against COS7 cells transfected with both UBE2T and HLA-A*0201 (black lozenge). On the other hand, no significant specific CTL activity was detected against target cells expressing either HLA-A*0201 (triangle) or UBE2T (circle).

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it should be understood that these descriptions are merely illustrative and not intended to be limited. It should also be understood that the present invention is not limited to the particular sizes, shapes, dimensions, materials, methodologies, protocols, etc. described herein, as these may vary in accordance with routine experimentation and optimization. Furthermore, the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to a peptide that are substantially free of cellular material such as carbohydrate, lipid, or other contaminating proteins from the cell or tissue source from which the peptide is derived, or substantially free of chemical precursors or other chemicals when chemically synthesized. The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamidegel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "oligopeptide" as used herein refers to a peptide which is composed of 20 amino acid residues or fewer, typically 15 amino acid residues or fewer. As used herein, the term "nonapeptide" refers to a peptide which is composed of 9 amino acid residues and the term "decapeptide" refers to a peptide which is composed of 10 amino acid resides.

The term "amino acid" as used herein refers to naturally occurring and synthetic amino acids, as well as amino acid analogs and amino acid mimetics that similarly function to the naturally occurring amino acids. Amino acids may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbone (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "polynucleotide", "oligonucleotide", and "nucleic acid" are used interchangeably herein and, unless otherwise specifically indicated, are referred to by their commonly accepted single-letter codes.

The term "agent" and "composition" are used interchangeably herein to refer to a product including the specified ingredients in the specified amounts, as well as any product that results, directly or indirectly, from combination of the specified ingredients in the specified amounts. Such terms, when used in relation to the modifier "pharmaceutical" (as in "pharmaceutical agent" and "pharmaceutical composition") are intended to encompass a product that includes the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the terms "pharmaceutical agent" and "pharmaceutical composition" refer to any product made by admixing a molecule or compound of the present invention and a pharmaceutically or physiologically acceptable carrier.

The term "active ingredient" herein refers to a substance in an agent or composition that is biologically or physiologically active. Particularly, in the context of pharmaceutical agent or composition, the term "active ingredient" refers to a substance that shows an objective pharmacological effect. For example, in case of pharmaceutical agents or compositions for use in the treatment or prevention of cancer, active ingredients in the agents or compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effects of active ingredients are inductions of CTLs that can recognize or kill cancer cells. Before being formulated, the "active ingredient" may also be referred to as "bulk", "drug substance" or "technical product".

The phrase "pharmaceutically acceptable carrier" or "physiologically acceptable carrier", as used herein, means a pharmaceutically or physiologically acceptable material, composition, substance or vehicle, including, but are not limited to, a liquid or solid filler, diluent, excipient, solvent and encapsulating material.

In some embodiments, pharmaceutical agents or compositions of the present invention find particular use as vaccines. In the context of the present invention, the term "vaccine" (also referred to as an "immunogenic composition") refers to an agent or composition that has the function to improve, enhance and/or induce anti-tumor immunity upon inoculation into animals.

Unless otherwise defined, the term "cancer" refers to cancers or tumors that overexpress the UBE2T gene, examples of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the term "HLA-A24", as used herein, representatively refers to the subtypes, examples of which include, but are not limited to, HLA-A*2401, HLA-A*2402, HLA-A*2403, HLA-A*2404, HLA-A*2407, HLA-A*2408, HLA-A*2420, HLA-A*2425 and HLA-A*2488.

Unless otherwise defined, the term "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "subject's (or patient's) HLA antigen is HLA-A24 or HLA-A2" refers to that the subject or patient homozygously or heterozygously possess HLA-A24 or HLA-A2 antigen gene, and HLA-A24 or HLA-A2 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as decrease in size, prevalence, or metastatic potential of cancer in a subject, prolongation of survival time, suppression of postoperative recurrence and so on. When the treatment is applied prophylactically, "efficacious" means that it retards or prevents cancer from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels". While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g., reducing the proliferation and metastasis of tumors.

In the context of the present invention, the treatment and/or prophylaxis of cancer and/or the prevention of post-operative recurrence thereof include any activity that leads to the following events, such as the surgical removal of cancer cells, the inhibition of the growth of cancerous cells, the involution or regression of a tumor, the induction of remission and suppression of occurrence of cancer, the tumor regression, and the reduction or inhibition of metastasis, the suppression of post operative recurrence of cancer, and prolongation of survival time. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis includes 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments as long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. Peptides

Peptides of the present invention described in detail below may be referred to as "UBE2T peptide(s) "or" UBE2T polypeptide(s)".

To demonstrate that peptides derived from UBE2T function as an antigen recognized by CTLs, peptides derived from UBE2T (SEQ ID NO: 65) were analyzed to determine whether they were antigen epitopes restricted by HLA-A24 or HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A24 binding peptides derived from UBE2T were identified based on their binding affinities to HLA-A24. The following candidate peptides were identified: SEQ ID NOs: 1, 2 and 4 to 27.

Moreover, after in vitro stimulation of T-cells by dendritic cells (DCs) pulsed (loaded) with these peptides, CTLs were successfully established using each of the following peptides:

UBE2T-A24-9-60 (SEQ ID NO: 1), UBE2T-A24-9-45 (SEQ ID NO: 2), UBE2T-A24-9-133 (SEQ ID NO: 4), UBE2T-A24-9-138 (SEQ ID NO: 6), UBE2T-A24-9-43 (SEQ ID NO: 11), UBE2T-A24-9-106 (SEQ ID NO: 12), UBE2T-A24-9-3 (SEQ ID NO: 13), UBE2T-A24-9-105 (SEQ ID NO: 15), UBE2T-A24-10-130 (SEQ ID NO: 17), UBE2T-A24-10-131 (SEQ ID NO: 19), UBE2T-A24-10-133 (SEQ ID NO: 20), UBE2T-A24-10-99 (SEQ ID NO: 21), UBE2T-A24-10-154 (SEQ ID NO: 22), UBE2T-A24-10-105 (SEQ ID NO: 23), UBE2T-A24-10-115 (SEQ ID NO: 24), UBE2T-A24-10-177 (SEQ ID NO: 25), and UBE2T-A24-10-44 (SEQ ID NO: 27).

Candidates of HLA-A2 binding peptides derived from UBE2T were identified based on their binding affinities to HLA-A2. The following peptides were identified: SEQ ID NOs: 29 to 63.

Moreover, after in vitro stimulation of T-cells by dendritic cells (DCs) pulsed (loaded) with these peptides, CTLs were successfully established using each of the following peptides:

UBE2T-A02-9-107 (SEQ ID NO: 29), UBE2T-A02-9-30 (SEQ ID NO: 30), UBE2T-A02-9-106 (SEQ ID NO: 32), UBE2T-A02-9-49 (SEQ ID NO: 36), UBE2T-A02-9-13 (SEQ ID NO: 38), UBE2T-A02-9-132 (SEQ ID NO: 41), UBE2T-A02-10-70 (SEQ ID NO: 48), UBE2T-A02-10-6 (SEQ ID NO: 49), UBE2T-A02-10-106 (SEQ ID NO: 51), UBE2T-A02-10-102 (SEQ ID NO: 52), UBE2T-A02-10-30 (SEQ ID NO: 53), UBE2T-A02-10-101 (SEQ ID NO: 55), UBE2T-A02-10-29 (SEQ ID NO: 56) and UBE2T-A02-10-38 (SEQ ID NO: 58).

These established CTLs show potent specific CTL activity against target cells pulsed with respective peptides. These results herein demonstrate that UBE2T is an antigen recognized by CTLs and that the above peptides are epitope peptides of UBE2T restricted by HLA-A24 or HLA-A2.

Accordingly, in preferred embodiments, peptides having the amino acid sequence of SEQ ID NO: 1, 2, 4, 6, 11, 12, 13, 15, 17, 19, 20, 21, 22, 23, 24, 25, or 27 may be used for the induction of CTLs in a subject that has been identified as having HLA-A24 prior to the induction. Likewise, peptides having the amino acid sequence of SEQ ID NO: 29, 30, 32, 36, 38, 41, 48, 49, 51, 52, 53, 55, 56 or 58 may be used for the induction of CTL in a subject that has been identified as having HLA-A2 prior to the induction.

Since the UBE2T gene is over-expressed in cancer cells and tissues, including for example those of bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor, and not expressed in most normal organs, it represents a good target for immunotherapy. Thus, the present invention provides nonapeptides (peptides composed of nine amino acid residues) and decapeptides (peptides composed of ten amino acid residues) corresponding to CTL-recognized epitopes from UBE2T. Alternatively, the present invention provides isolated peptides which can induce CTLs, wherein the peptide is composed of an immunologically active fragment of UBE2T. In some embodiments, the present invention provides peptides including an amino acid sequence selected from among SEQ TD NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58. In preferred embodiments, the peptides of the present invention are nonapeptides or decapeptides including an amino acid sequence selected from among SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58. The preferred examples of the peptides of the present invention include peptides consisting of an amino acid sequence selected from among SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58.

The peptides of the present invention, particularly the nonapeptides and decapeptides of the present invention, may be flanked with additional amino acid residues, as long as the resulting peptide retains its CTL inducibility. The particular additional amino acid residues may be composed of any kind of amino acids, as long as they do not impair the CTL inducibility of the original peptide. Thus, the present invention encompasses peptides having CTL inducibility, in particular peptides derived from UBE2T (e.g., peptides including the amino acid sequence of SEQ ID NO: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 or 58). Such peptides are, for example, less than about 40 amino acids, often less than about 20 amino acids, and usually less than about 15 amino acids. More specifically, the size of such peptide is preferably in the range of 10 to 40 amino acids, such as in the range of 10 to 20 amino acids, for example in the range 10 to 15 amino acids.

Generally, it is known that the modification of one, two or several amino acids in a peptide do not influence the function of the peptide, and in some cases even enhance the desired function of the original peptide. In fact, modified peptides (i.e., peptides composed of an amino acid sequence in which 1, 2 or several amino acid residues have been modified (i.e., substituted, added, deleted and/or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention have both CTL inducibility and an amino acid sequence selected from among SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58, in which one, two or several amino acids are added, deleted, inserted and/or substituted. In other words, the peptides of the present invention have both CTL inducibility and an amino acid sequence in which one, two or several amino acid(s) are substituted, deleted, inserted and/or added in the amino acid sequence selected from among SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58, provided the modified peptides retain the CTL inducibility of the original peptide.

Those of skill in the art will recognize that individual modifications (i.e., deletions, insertions, additions and/or substitutions) to an amino acid sequence that alter a single amino acid or a small percentage of the overall amino acid sequence tend to result in the conservation of the properties of the original amino acid side-chain. As such, they are conventionally referred to as "conservative substitutions" or "conservative modifications", wherein the alteration of a protein results in a protein with similar functions to the original protein. Conservative substitution tables providing functionally similar amino acids are well known in the art. Examples of amino acid side-chains characteristics that are desirable to conserve include, for example: hydrophobic amino acids (A, I, L, M, F, P, W, Y, V), hydrophilic amino acids (R, D, N, C, E, Q, G, H, K, S, T), and side-chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, peptides of the present invention are not restricted thereto and may include non-conservative modifications, as long as the resulting modified peptide retains the requisite CTL inducibility of the original unmodified peptide. Furthermore, the modified peptides should not exclude CTL inducible peptides derived from polymorphic variants, interspecies homologues, and alleles of UBE2T.

Amino acid residues may be inserted, substituted and/or added to the peptides of the present invention or, alternatively, amino acid residues may be deleted therefrom to achieve a higher binding affinity. To retain the requisite CTL inducibility, one of skill in the art preferably modifies (i.e., deletes, inserts, adds and/or substitutes) only a small number (for example, 1, 2 or several) or a small percentage of amino acids. Herein, the term "several" means 5 or fewer amino acids, for example, 4 or 3 or fewer. The percentage of amino acids to be modified may be, for example, 30% or less, preferably 20% or less, more preferably 15% or less, and even more preferably 10% or less, for example 1 to 5%.

When used in the context of cancer immunotherapy, the peptides of the present invention may be presented on the surface of a cell or exosome as a complex with an HLA antigen. Therefore, it is preferable to select peptides that not only induce CTLs but also possess high binding affinity to the HLA antigen. To that end, the peptides can be modified by substitution, insertion, deletion and/or addition of the amino acid residues to yield a modified peptide having improved binding affinity to the HLA antigen. In addition to peptides that are naturally displayed, since the regularity of the sequences of peptides displayed by binding to HLA antigens has already been known (Kubo R T et al., J Immunol 1994, 152: 3913-24; Rammensee H G et al., Immunogenetics 1995, 41: 178-228; Kondo et al., J Immunol 1994, 155: 4307-12; Falk K, et al., Nature. 1991 May 23; 351(6324):290-6.), modifications based on such regularity may be introduced into the immunogenic peptides of the present invention.

For example, peptides possessing high HLA-A24 binding affinity tend to have the second amino acid from the N-terminus substituted with phenylalanine, tyrosine, methionine or tryptophan. Likewise, peptides in which the C-terminal amino acid is substituted with phenylalanine, leucine, isoleucine, tryptophan or methionine tend to have high HLA-A24 binding affinity. Accordingly, it may be desirable to substitute the second amino acid from the N-terminus with phenylalanine, tyrosine, methionine or tryptophan, and/or the amino acid at the C-terminus with leucine, isoleucine, tryptophan or methionine in order to increase the HLA-A24 binding affinity. Thus, peptides having an amino acid sequence selected from among SEQ ID NOs: 1, 2, 4, 6, 11, 12, 13, 15, 17, 19, 20, 21, 22, 23, 24, 25, and 27, in which the second amino acid from the N-terminus of the amino acid sequence of the SEQ ID NO is substituted with phenylalanine, tyrosine, methionine or tryptophan, and/or in which the C-terminus of the amino acid sequence of the SEQ ID NO is substituted with leucine, isoleucine, tryptophan or methionine are encompassed by the present invention. Also, the present invention encompasses the peptides including an amino acid sequence in which one, two or several amino acid are substituted, deleted, inserted and/or added in the SEQ ID NOs: 1, 2, 4, 6, 11, 12, 13, 15, 17, 19, 20, 21, 22, 23, 24, 25, and 27, such peptides having one or both of the following characteristic of (a) the second amino acid from the N-terminus is phenylalanine, tyrosine, methionine or tryptophan; and (b) the C-terminal amino acid is phenylalanine, leucine, isoleucine, tryptophan or methionine. In preferred embodiments, the peptides of the present invention include an amino acid sequence in which the second amino acid from the N-terminus is substituted with phenylalanine, tyrosine, methionine or tryptophan, and/or the C-terminal amino acid is substituted with phenylalanine, leucine, isoleucine, tryptophan or methionine in the amino acid sequence of SEQ ID NOs: 1, 2, 4, 6, 11, 12, 13, 15, 17, 19, 20, 21, 22, 23, 24, 25, and 27.

Likewise, peptides possessing high HLA-A2 binding affinity tend to have the second amino acid from the N-terminus substituted with leucine or methionine and/or the amino acid at the C-terminus substituted with valine or leucine. Accordingly, it may be desirable to substitute the second amino acid from the N-terminus with leucine or methionine, and/or the amino acid at the C-terminus with valine or leucine in order to increase the HLA-A2 binding affinity. Thus, peptides having an amino acid sequence selected from among SEQ ID NOs: 29, 30, 32, 36, 38, 41, 48, 49, 51, 52, 53, 55, 56 and 58, in which the second amino acid from the N-terminus of the amino acid sequence of the SEQ ID NO is substituted with leucine or methionine, and/or wherein the C-terminus of the amino acid sequence of the SEQ ID NO is substituted with valine or leucine are encompassed by the present invention. Also, the present invention encompasses the peptides including an amino acid sequence in which one, two or several amino acid are substituted, deleted, inserted and/or added in the SEQ ID NOs: 29, 30, 32, 36, 38, 41, 48, 49, 51, 52, 53, 55, 56 and 58, such peptides having one or both of the following characteristic of (a) the second amino acid from the N-terminus is leucine or methionine; and (b) the C-terminal amino acid is valine or leucine. In preferred embodiments, the peptides of the present invention include an amino acid sequence in which the second amino acid from the N-terminus is substituted with leucine or methionine, and/or the C-terminal amino acid is substituted with valine or leucine in the amino acid sequence of SEQ ID NOs: 29, 30, 32, 36, 38, 41, 48, 49, 51, 52, 53, 55, 56 and 58.

Substitutions can be introduced not only at the terminal amino acids but also at the positions of potential T cell receptor (TCR) recognition sites of peptides. Several studies have demonstrated that a peptide with amino acid substitutions may have equal to or better function than that of the original, for example, CAP1, p53$_{(264-272)}$, Her-2/neu$_{(369-377)}$ or gp 100$_{(209-217)}$ (Zaremba et al. Cancer Res. 57, 4570-4577, 1997, Hoffmann T K et al. J Immunol. (2002); 168(3):1338-47., Dionne S O et al. Cancer Immunol immunother. (2003) 52: 199-206 and Dionne S O et al. Cancer Immunology, Immunotherapy (2004) 53, 307-314).

The present invention also contemplates the addition of 1, 2 or several amino acids can also be added to the N and/or C-terminus of the peptides of the present invention. Such modified peptides having CTL inducibility are also included in the present invention.

For example, the present invention provides an isolated peptide of less than 15, 14, 13, 12, 11, or 10 amino acids in length, which has CTL inducibility and comprises the amino acid sequence selected from the group consisting of:

(i) an amino acid sequence in which 1, 2 or several amino acid(s) are modified in the amino acid sequence selected from the group consisting of SEQ ID NOs: 1, 2, 4, 6, 11, 12, 13, and 15, (ii) the amino acid sequence of (i), wherein the amino acid sequence has one or both of the following characteristics:
(a) the second amino acid from the N-terminus of said SEQ ID NOs is or is modified to be an amino acid selected from the group consisting of phenylalanine, tyrosine, methionine and tryptophan, and (b) the C-terminal amino acid of said SEQ ID NOs is or is modified to be an amino acid selected from the group consisting of phenylalanine, leucine, isoleucine, tryptophan and methionine, and (iii) the amino acid sequence in which 1, 2 or several amino acid(s) are modified in the amino acid sequence selected from the group consisting of SEQ ID NOs: 29, 30, 32, 36, 38, and 41

(iv) the amino acid sequence of (iii), wherein the amino acid sequence has one or both of the following characteristics:

(a) the second amino acid from the N-terminus of said SEQ ID NO is or is modified to be an amino acid selected from the group consisting of leucine and methionine; and (b) the C-terminal amino acid of said SEQ ID NO is or is modified to be an amino acid selected from the group consisting of valine and leucine.

Moreover, the present invention also provides an isolated peptide of less than 15, 14, 13, 12, or 11 amino acids in length, which has CTL inducibility and comprises the amino acid sequence selected from the group consisting of:

(i') an amino acid sequence in which 1, 2 or several amino acid(s) are modified in the amino acid sequence selected from the group consisting of SEQ ID NOs: 17, 19, 20, 21, 22, 23, 24, 25, and 27, (ii') the amino acid sequence of (i'), wherein the amino acid sequence has one or both of the following characteristics:

(a) the second amino acid from the N-terminus of said SEQ ID NOs is or is modified to be an amino acid selected from the group consisting of phenylalanine, tyrosine, methionine and tryptophan, and (b) the C-terminal amino acid of said SEQ ID NOs is or is modified to be an amino acid selected from the group consisting of phenylalanine, leucine, isoleucine, tryptophan, and methionine, (iii') an amino acid sequence in which 1, 2 or several amino acid(s) are modified in the amino acid sequence selected from the group consisting of SEQ ID NOs: 48, 49, 51, 52, 53, 55, 56 and 58, (iv') the amino acid sequence of (iii'), wherein the amino acid sequence has one or both of the following characteristics:

(a) the second amino acid from the N-terminus of said SEQ ID NOs is or is modified to be an amino acid selected from the group consisting of leucine and methionine; and (b) the C-terminal amino acid of said SEQ ID NOs is or is modified to be an amino acid selected from the group consisting of valine and leucine.

These peptides are processed in an APC to present a peptide selected from the group consisting of (i) to (iv) and (i') to (iv') thereon, when these peptides are contacted with, or introduced in APC.

However, when the peptide sequence is identical to a portion of the amino acid sequence of an endogenous or exogenous protein having a different function, side effects such as autoimmune disorders and/or allergic symptoms against specific substances may be induced. Therefore, it is preferable to first perform homology searches using available databases to avoid situations in which the sequence of the peptide matches the amino acid sequence of another protein. When it becomes clear from the homology searches that there exists not even a peptide with 1 or 2 amino acid differences as compared to the objective peptide, the objective peptide can be modified in order to increase its binding affinity with HLA antigens, and/or increase its CTL inducibility without any danger of such side effects.

Although peptides having high binding affinity to the HLA antigens are expected to be effective, the candidate peptides, which are selected according to the presence of high binding affinity as an indicator, are further examined for the presence of CTL inducibility. Herein, the phrase "CTL inducibility" indicates the ability of a peptide to induce a cytotoxic T lymphocyte (CTL) when presented on an antigen-presenting cell (APC). Further, "CTL inducibility" includes the ability of a peptide to induce CTL activation, CTL proliferation, promote lysis of target cells by a CTL, and to increase IFN-gamma production by a CTL.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation of APCs with a test peptides, mixing the APCs with CD8 positive T cells to induce CTLs, and then measuring the IFN-gamma against the target cells produced and released by CTLs. As the reaction system, transgenic animals that have been produced to express a human HLA antigen (for example, those described in BenMohamed L et al., Hum Immunol 2000, 61(8): 764-79, Related Articles, Books, Linkout Induction of CTL response by a minimal epitope vaccine in HLA-A*0201/DR1 transgenic mice: dependence on HLA class II restricted T(H) response) can be used. Alternatively, the target cells may be radiolabeled with $^{51}$Cr and such, and cytotoxic activity of CTLs may be calculated from radioactivity released from the target cells. Alternatively, CTL inducibility can be assessed by measuring IFN-gamma produced and released by CTLs in the presence of cells that carry immobilized peptides, and visualizing the inhibition zone on the media using anti-IFN-gamma monoclonal antibodies.

In addition to the above-described modifications, the peptides of the present invention can also be linked to other peptides, as long as the resulting linked peptide retains the requisite CTL inducibility of the original peptide, and more preferably also retains the requisite HLA binding ability thereof. Examples of suitable "other" peptides include: the peptides of the present invention or the CTL-inducible peptides derived from other TAAs. The peptide of the present invention can be linked to "another" peptide directly or indirectly via a linker. The linkers between the peptides are well known in the art and include, for example AAY (Daftarian P M, et al., J Trans Med 2007, 5:26), AAA, NKRK (Sutmuller R P, et al., J Immunol. 2000, 165: 7308-7315) or K (Ota S, et al., Can Res. 62, 1471-1476, Kawamura K S, et al., J Immunol. 2002, 168: 5709-5715).

The above described linked peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in accordance with a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci USA 92(13):5845-5849, 1995; Gilbert et al., Nature Biotechnol. 15(12):1280-1284, 1997; Thomson et al., J Immunol. 157(2):822-826, 1996; Tarn et al., J Exp. Med. 171(1):299-306, 1990). Polytopes containing various numbers and combinations of epitopes can be prepared and tested for recognition by CTLs and for efficacy in increasing an immune response.

The peptides of the present invention may also be linked to other substances, as long as the resulting linked peptide retains the requisite CTL inducibility of the original peptide. Examples of suitable substances include, for example: peptides, lipids, sugar and sugar chains, acetyl groups, natural and synthetic polymers, etc. The peptides may contain modifications such as glycosylation, side chain oxidation, or phosphorylation, etc., provided the modifications do not destroy the biological activity of the original peptide. These kinds of modifications may be performed to confer additional functions (e.g., targeting function, and delivery function) or to stabilize the peptide.

For example, to increase the in vivo stability of a peptide, it is known in the art to introduce D-amino acids, amino acid mimetics or unnatural amino acids; this concept can also be adapted to the peptides of the present invention. The stability of a peptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides in which are substituted, deleted inserted and/or added by 1, 2 or several amino acid residues, those having same or higher activity as compared to original peptides can be screened for or selected. The present invention, therefore, also provides the method of screening for or selecting modified peptides having same or higher activity as compared to originals. An illustrative method includes the steps of:

a: substituting, deleting, inserting and/or adding at least one amino acid residue of a peptide of the present invention, b: determining the activity of the peptide modified in step a, and c: selecting the peptide having same or higher activity as compared to the original peptide.

Preferably, the activity of the peptide to be assayed is CTL inducibility.

In preferred embodiments, the present invention provides a method of screening for a peptide having an ability to induce a CTL that has specific cytotoxic activity against a cell that presents a fragment derived from UBE2T, wherein the method comprises the steps of:

(i) providing a candidate sequence consisting of an amino acid sequence modified by substituting, deleting, inserting and/or adding one, two or several amino acid residues to an original amino acid sequence, wherein the original amino acid sequence is selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58;

(ii) selecting a candidate sequence that does not have substantial significant homology (or sequence identity) with the peptides derived from any known human gene products other than UBE2T;

(iii) contacting a peptide consisting of the candidate sequence selected in step (ii) with an antigen presenting cell;

(iv) contacting the antigen presenting cell of step (iii) with a CD8 positive T cell; and (v) identifying the peptide of which CTL inducibility is same to or higher than a peptide consisting of the original amino acid sequence.

III. Preparation of UBE2T Peptides

The peptides of the present invention can be prepared using well known techniques. For example, the peptides can be prepared synthetically, using recombinant DNA technology or chemical synthesis. The peptides of the present invention can be synthesized individually or as longer polypeptides including two or more peptides. The peptides can then be isolated i.e., purified or isolated so as to be substantially free of other naturally occurring host cell proteins and fragments thereof, or any other chemical substances.

The peptides of the present invention may contain modifications, such as glycosylation, side chain oxidation, or phosphorylation, provided the modifications do not destroy the biological activity of the original peptide. Other illustrative modifications include incorporation of one or more D-amino acids or other amino acid mimetics that can be used, for example, to increase the serum half life of the peptides.

Peptides of the present invention can be obtained through chemical synthesis based on the selected amino acid sequence. For example, conventional peptide synthesis methods that can be adopted for the synthesis include:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the peptides of the present invention can be obtained adopting any known genetic engineering method for producing peptides (e.g. Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g. downstream of a regulatory sequence corresponding to a promoter sequence) is prepared and transformed into a suitable host cell. Such vectors and host cells are also provided by the present invention. The host cell is then cultured to produce the peptide of interest. The peptide can also be produced in vitro adopting an in vitro translation system.

IV. Polynucleotides

The present invention also provides polynucleotides that encode any of the aforementioned peptides of the present invention. These include polynucleotides derived from the natural occurring UBE2T gene (e.g., GenBank Accession No. NM_014176 (SEQ ID NO: 64)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. As is well known in the art, a DNA is suitably composed of bases such as A, T, C, and G, and T is replaced by U in an RNA. One of skill in the art will recognize that non-naturally occurring bases may be included in polynucleotides, as well.

The polynucleotide of the present invention can encode multiple peptides of the present invention with or without intervening amino acid sequences. For example, the intervening amino acid sequence can provide a cleavage site (e.g., enzyme recognition sequence) of the polynucleotide or the translated peptides. Furthermore, the polynucleotide of the present invention can include any additional sequences to the coding sequence encoding the peptide of the present invention. For example, the polynucleotide of the present invention can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, the polynucleotide of the present invention can be produced by insertion into an appropriate vector, which can be expressed when transfected into a competent cell. Alternatively, the polynucleotide of the present invention can be amplified using PCR techniques or expression in suitable hosts (see, e.g., Sambrook et al., Molecular Cloning: A Laboratory Manual, Cold Spring Harbor Laboratory, New York, 1989). Alternatively, the polynucleotide of the present invention can be synthesized using the solid phase techniques, as described in Beaucage S L & Iyer R P, Tetrahedron 1992, 48: 2223-311; Matthes et al., EMBO J 1984, 3: 801-5.

V. Exosomes

The present invention further provides intracellular vesicles called exosomes, which present complexes formed between the peptides of the present invention and HLA antigens on their surface. Exosomes can be prepared, for example, using the methods detailed in Japanese Patent Publication No. H11-510507 and WO99/03499, and can be prepared using APCs obtained from patients who are subject to treatment and/or prevention. The exosomes of the present invention can be inoculated as vaccines, in a fashion similar to the peptides of the present invention.

The type of HLA antigens included in the complexes must match that of the subject requiring treatment and/or prevention. For example, in the Japanese population, HLA-A24 and HLA-A2, particularly HLA-A*2402 and HLA-A*0201 and HLA-A*0206, are prevalent and therefore would be appropriate for treatment of Japanese patients. The use of the HLA-A24 or HLA-A2 type that are highly expressed among the Japanese and Caucasian is favorable for obtaining effective results, and subtypes such as HLA-A*2402, HLA-A*0201 and HLA-A*0206 also find use. Typically, in the clinic, the type of HLA antigen of the patient requiring treatment is investigated in advance, which enables the appropriate selection of peptides having high levels of binding affinity to the particular antigen, or having CTL inducibility by antigen presentation. Furthermore, in order to obtain peptides having both high binding affinity and CTL inducibility, substitution, insertion, deletion and/or addition of 1, 2, or several amino acids can be performed based on the amino acid sequence of the naturally occurring UBE2T partial peptide.

When using the HLA-A24 type of HLA antigen for the exosome of the present invention, peptides having an amino acid sequence selected from among SEQ ID NOs: 1, 2, 4, 6, 11, 12, 13, 15, 17, 19, 20, 21, 22, 23, 24, 25 and 27 have particular utility.

Alternatively, when using the HLA-A2 type of HLA antigen for the exosome of the present invention, peptides having an amino acid sequence selected from among SEQ ID NOs: 29, 30, 32, 36, 38, 41, 48, 49, 51, 52, 53, 55, 56 and 58 have particular utility.

In some embodiments, the exosomes of the present invention present a complex of the peptide of the present invention and HLA-A24 or HLA-A2 antigen on their surface. In typical embodiments, the exosome of the present invention presents a complex of a peptide having an amino acid sequence of SEQ ID NO: 1, 2, 4, 6, 11, 12, 13, 15, 17, 19, 20, 21, 22, 23, 24, 25 or 27 (or modified peptide thereof) and HLA-A24 on its surface. In other embodiments, the exosome of the present invention presents a complex of a peptide having an amino acid sequence of SEQ ID NO: 29, 30, 32, 36, 38, 41, 48, 49, 51, 52, 53, 55, 56 or 58 (or modified peptide thereof) and HLA-A2 on its surface.

VI. Antigen-Presenting Cells (APCs)

The present invention also provides isolated antigen-presenting cells (APCs) that present complexes formed between HLA antigens and the peptides of the present invention on their surface. The APCs can be derived from patients who are subject to treatment and/or prevention, and can be administered as vaccines by themselves or in combination with other drugs including the peptides, exosomes, or CTLs of the present invention.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DCs are representative APCs having the strongest CTL inducing activity among APCs, DCs are suitable for the APCs of the present invention.

For example, the APCs of the present invention can be obtained by inducing DCs from peripheral blood monocytes and then contacting (stimulating) them with the peptides of the present invention in vitro, ex vivo or in vivo. When the peptides of the present invention are administered to a subject, APCs that present the peptides of the present invention are induced in the body of the subject. Therefore, the APCs of the present invention can be obtained by collecting the APCs from a subject after administering the peptides of the present invention to the subject. Alternatively, the APCs of the present invention can be obtained by contacting APCs, which have been collected from a subject, with the peptide of the present invention.

The APCs of the present invention can be administered to a subject for inducing immune response against cancer in the subject by themselves or in combination with other drugs including the peptides, exosomes or CTLs of the present invention. For example, the ex vivo administration can include steps of:

a: collecting APCs from a first subject,
b: contacting the APCs of step a, with the peptide of the present invention, and
c: administering the APCs of step b to a second subject.

The first subject and the second subject can be the same individual, or may be different individuals. The APCs obtained by step b can be formulated and administered a vaccine for treating and/or preventing cancer, such as bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor, but not limited thereto.

In the context of the present invention, one may utilize the peptides of the present invention for manufacturing a pharmaceutical composition capable of inducing an antigen-presenting cell. The present invention also provides a method or process for manufacturing a pharmaceutical composition for inducing an antigen-presenting cell wherein the method includes the step of admixing or formulating the peptide of the invention with a pharmaceutically acceptable carrier.

The present invention also provides for the use of the peptides of the present invention for inducing antigen-presenting cells.

According to an aspect of the present invention, the APCs of the present invention have CTL inducibility. In the context of the APCs, the phrase "CTL inducibility" refers to the ability of an APC to induce a CTL when contacted with a CD8 positive T cell. Further, "CTL inducibility" includes the ability of an APC to induce CTL activation, CTL proliferation, promote lysis of a target cell by a CTL, and to increase IFN-gamma production by a CTL. In particular, the APCs of the present invention have an ability to induce CTLs specific to UBE2T. Such APCs having CTL inducibility can be prepared by a method that includes the step of transferring a polynucleotide encoding the peptide of the present invention to APCs in vitro as well as the method mentioned above. The introduced gene can be in the form of DNA or RNA. Examples of methods for introduction include, without particular limitations, various methods conventionally performed in this field, such as lipofection, electroporation, and calcium phosphate method can be used. More specifically, it can be performed as described in Reeves M E et al., Cancer Res 1996, 56: 5672-7; Butterfield L H et al., J Immunol 1998, 161: 5607-13; Boczkowski D et al., J Exp Med 1996, 184: 465-72; Japanese Patent Publication No. JP2000-509281. By transferring the gene into APCs, the gene undergoes transcription, translation, and such in the cell, and then the obtained protein is processed by MHC Class I or Class II, and proceeds through a presentation pathway to present partial peptides.

In some embodiments, the APCs of the present invention present complexes of HLA-A24 or HLA-A2 antigen and the peptide of the present invention on their surface. In typical embodiments, the APC of the present invention presents a complex of a peptide having an amino acid sequence of SEQ ID NO: 1, 2, 4, 6, 11, 12, 13, 15, 17, 19, 20, 21, 22, 23, 24, 25, or 27 (or modified peptide thereof) and HLA-A24 on its surface. In other embodiments, the APC of the present invention presents a complex of a peptide having an amino acid sequence of SEQ ID NO: 29, 30, 32, 36, 38, 41, 48, 49, 51, 52, 53, 55, 56 or 58 (or modified peptide thereof) and HLA-A2 on its surface.

VII. Cytotoxic T Lymphocytes (CTLs)

A CTL induced against any one of the peptides of the present invention strengthens the immune response targeting cancer cells in vivo and thus can be used as vaccines, in a fashion similar to the peptides per se. Thus, the present invention provides isolated CTLs that are specifically induced or activated by any one of the peptides of the present invention.

Such CTLs can be obtained by (1) administering the peptide(s) of the present invention to a subject, (2) contacting (stimulating) subject-derived APCs, and CD8 positive T cells, or peripheral blood mononuclear leukocytes in vitro with the peptide(s) of the present invention, (3) contacting CD8 positive T cells or peripheral blood mononuclear leukocytes in vitro with the APCs or exosomes presenting a complex of an HLA antigen and the peptide on its surface or (4) introducing into a CD8 positive T cell a polynucleotide encoding both of T cell receptor (TCR) subunits or polynucleotides encoding each of TCR subunits, wherein the TCR formed by such subunits can bind a complex of the peptide of the present invention and HLA antigen on a cell surface. Such APCs or exosomes can be prepared by the methods described above. Details of the method of (4) are described bellow in section "VIII. T Cell Receptor (TCR)".

The CTLs of the present invention can be derived from patients who are subject to treatment and/or prevention, and can be administered by themselves or in combination with other drugs including the peptides, APCs or exosomes of the present invention for the purpose of regulating effects. The obtained CTLs act specifically against target cells presenting the peptides of the present invention, for example, the same peptides used for induction. The target cells can be cells that endogenously express UBE2T, such as cancer cells, or cells that are transfected with the UBE2T gene; and cells that present a peptide of the present invention on the cell surface due to stimulation by the peptide can also serve as targets of activated CTL attack.

In some embodiments, the CTLs of the present invention are CTLs that recognize cells presenting complexes of an HLA-A24 or HLA-A2 antigen and the peptide of the present invention. In the context of CTLs, the phrase "recognize a cell" refers to binding a complex of an HLA-A24 or HLA-A2 antigen and the peptide of the present invention on the cell surface via its TCR and showing specific cytotoxic activity against the cell. Herein, "specific cytotoxic activity" refers to showing cytotoxic activity against a cell presenting a complex of an HLA-A24 or HLA-A2 antigen and the peptide of the present invention but not other cells. Accordingly, the CTLs that show specific cytotoxic activity against a cell presenting the peptide of the present invention are included in the present invention.

In typical embodiments, the CTL of the present invention can recognize a cell presenting a peptide having an amino acid sequence of SEQ ID NO: 1, 2, 4, 6, 11, 12, 13, 15, 17, 19, 20, 21, 22, 23, 24, 25 or 27 (or modified peptide thereof) via an HLA-A24. In preferred embodiments, such CTL of the present invention can recognize a cell expressing UBE2T and an HLA-A24 (e.g., HLA-A24 positive cancer cell) and show cytotoxic activity against such cell.

In other embodiments, the CTL of the present invention can recognize a cell presenting a peptide having an amino acid sequence of SEQ ID NO: 29, 30, 32, 36, 38, 41, 48, 49, 51, 52, 53, 55, 56 or 58 (or modified peptide thereof) via an HLA-A2. In preferred embodiments, such CTL of the present invention can recognize a cell expressing UBE2T and an HLA-A2 (e.g., HLA-A2 positive cancer cell) and show cytotoxic activity against such cell.

VIII. T Cell Receptor (TCR)

The present invention also provides a composition including a polynucleotide encoding both of TCR subunits or polynucleotides encoding each of TCR subunits, wherein the TCR formed by such subunits can bind to a complex of an HLA antigen and the peptide of the present invention on a cell surface, and methods of using the same. The TCR subunits have the ability to form TCRs that confer specificity to T cells against tumor cells expressing UBE2T. By using known methods in the art, the polynucleotides encoding each of alpha- and beta-chains of the TCR subunits of the CTL induced with one or more peptides of the present invention can be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') as 5' side primers (SEQ ID NO: 66) and 3-TRa-C primers (5'-tcagctggaccacagccgcagcgt-3') specific to TCR alpha chain C region (SEQ ID NO: 67), 3-TRb-C1 primers (5'-tcagaaatcctttctcttgac-3') specific to TCR beta chain C1 region (SEQ ID NO: 68) or 3-TRbeta-C2 primers (5'ctagcctctggaatcctttctctt-3') specific to TCR beta chain C2 region (SEQ ID NO: 69) as 3' side primers, but not limited thereto. The derivative TCRs can bind target cells presenting the peptide of the present invention with high avidity, and optionally mediate efficient killing of target cells presenting the peptide of the present invention in vivo and in vitro.

The polynucleotide encoding both of the TCR subunits or polynucleotides encoding each of the TCR subunits can be incorporated into suitable vectors, e.g., retroviral vectors. These vectors are well known in the art. The polynucleotides or the vectors including them usefully can be transferred into a T cell (e.g., CD8 positive T cell), for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR against the peptide of the present invention is a receptor capable of specifically recognizing a complex of a peptide of the present invention and an HLA molecule, giving a T cell specific activity against a target cell presenting a complex of the peptide of the present invention and an HLA antigen when the TCR is presented on the surface of the T cell. A specific recognition of the above complex may be confirmed by any known methods, preferred examples of which include HLA multimer staining analysis using HLA molecules and peptides of the present invention, and ELISPOT assay. By performing the ELISPOT assay, it can be confirmed that a T cell expressing the TCR on the cell surface recognizes a cell by the TCR, and that signals are transmitted intracellularly. The confirmation that the above-mentioned TCR can give a T cell cytotoxic activity when the TCR exists on the T cell surface may also be carried out by a known method. A preferred method includes, for example, the determination of cytotoxic activity against a target cell, such as chromium release assay.

Also, the present invention provides CTLs which are prepared by transduction with the polynucleotides encoding both of the TCR subunits or polynucleotides encoding each of the TCR subunits wherein the TCR formed by such TCR subunits can bind to the UBE2T peptide, e.g., a peptide having the amino acid sequence of SEQ ID NO: 1, 2, 4, 6, 11, 12, 13, 15, 17, 19, 20, 21, 22, 23, 24, 25 or 27, in the context of HLA-A24, and also a peptide having the amino acid sequence of SEQ ID NO: 29, 30, 32, 36, 38, 41, 48, 49, 51, 52, 53, 55, 56 or 58, in the context of HLA-A2.

The transduced CTLs are capable of homing to cancer cells in vivo, and can be expanded by well known culturing methods in vitro (e.g., Kawakami et al., J Immunol., 142, 3452-3461 (1989)). The CTLs of the present invention can be used to form an immunogenic composition useful in either or both of treatment and the prevention of cancer in a patient in need of therapy or protection (See, WO2006/031221, the contents of which are incorporated by reference herein).

IX. Pharmaceutical Agents or Compositions

The present invention also provides pharmaceutical agents or compositions including at least one active ingredient selected from among:
(a) a peptide of the present invention;
(b) a polynucleotide encoding such a peptide of the present invention in an expressible form;
(c) an APC of the present invention;
(d) an exosome of the present invention; and
(e) a CTL of the present invention.

Since UBE2T expression is specifically elevated in cancers, examples of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor, the peptides or polynucleotides of the present invention may be used for the treatment and/or prophylaxis of cancer, and/or for the prevention of a postoperative recurrence thereof. Thus, the present invention provides a pharmaceutical composition or agent formulated for the treatment and/or prophylaxis of cancer, and/or for the prevention of a postoperative recurrence thereof, such composition or agent including at least one of the peptides or polynucleotides of the present invention as an active ingredient. Alternatively, the peptides of the present invention can be expressed on the surface of any of the foregoing exosomes or cells, such as APCs for the use as pharmaceutical compositions or agents. In addition, the aforementioned CTLs which target any one of the peptides of the present invention can also be used as the active ingredient of the pharmaceutical compositions or agents of the present invention.

Accordingly, the present invention provides agents or compositions including at least one active ingredient selected from among:
(a) a peptide of the present invention;
(b) a polynucleotide encoding such a peptide of the present invention in an expressible form;
(c) an APC of the present invention;
(d) an exosome of the present invention; and
(e) a CTL of the present invention.

In the pharmaceutical agent or composition, such active ingredient is present in a therapeutically or pharmaceutically effective amount.

The pharmaceutical composition or agent of the present invention also find use as a vaccine. In the context of the present invention, the phrase "vaccine" (also referred to as an "immunogenic composition") refers to an agent or composition that has the function to improve, enhance and/or induce anti-tumor immunity upon inoculation into an animal. In other words, the present invention provides the pharmaceutical agents or compositions for inducing an immune response against cancer in a subject. The amount of the peptide in such agent or composition may be an amount that is effective in significantly enhancing or stimulating immunological response in a subject carrying a cancer expressing UBE2T.

The pharmaceutical compositions or agents of the present invention can be used to treat and/or prevent cancers, and/or prevent a postoperative recurrence thereof in subjects or patients including human and any other mammals including, but not limited to, mice, rats, guinea-pigs, rabbits, cats, dogs, sheep, goats, pigs, cattle, horses, monkeys, baboons, and chimpanzees, particularly commercially important animals or domesticated animals. In some embodiments, the pharmaceutical agents or compositions of the present invention can be formulated for the administration to a subject whose HLA antigen is HLA-A24 or HLA-A2.

In another embodiment, the present invention also provides the use of an active ingredient in manufacturing a pharmaceutical composition or agent for treating and/or preventing cancer or tumor, and/or preventing a post-operative recurrence thereof, said active ingredient selected from among:
  (a) a peptide of the present invention;
  (b) a polynucleotide encoding such a peptide of the present invention in an expressible form;
  (c) an APC presenting a peptide of the present invention on its surface;
  (d) an exosome presenting a peptide of the present invention on its surface; and
  (e) a CTL of the present invention.

Alternatively, the present invention further provides an active ingredient for use in the treatment and/or prevention of cancers or tumors, and/or prevention of a postoperative recurrence thereof, said active ingredient selected from among:
  (a) a peptide of the present invention;
  (b) a polynucleotide encoding such a peptide of the present invention in an expressible form;
  (c) an APC presenting a peptide of the present invention on its surface;
  (d) an exosome presenting a peptide of the present invention on its surface; and
  (e) a CTL of the present invention.

Alternatively, the present invention further provides a method or process for manufacturing a pharmaceutical composition or agent for treating and/or preventing cancer or tumor, and/or preventing a post-operative recurrence thereof, wherein the method or process includes the step of formulating a pharmaceutically or physiologically acceptable carrier with an active ingredient selected from among:
  (a) a peptide of the present invention;
  (b) a polynucleotide encoding such a peptide of the present invention in an expressible form;
  (c) an APC presenting a peptide of the present invention on its surface;
  (d) an exosome presenting a peptide of the present invention on its surface; and
  (e) a CTL of the present invention.

In another embodiment, the present invention also provides a method or process for manufacturing a pharmaceutical composition or agent for treating and/or preventing cancer or tumor, and/or preventing a post-operative recurrence thereof, wherein the method or process includes the steps of admixing an active ingredient with a pharmaceutically or physiologically acceptable carrier, wherein the active ingredient is selected from among:
  (a) a peptide of the present invention;
  (b) a polynucleotide encoding such a peptide of the present invention in an expressible form;
  (c) an APC presenting a peptide of the present invention on its surface;
  (d) an exosome presenting a peptide of the present invention on its surface; and
  (e) a CTL T cell of the present invention.

In another embodiment, the present invention also provides a method for treating and/or preventing cancer or tumor, and/or preventing a post-operative recurrence thereof, wherein the method comprises the step of administering to a subject at least one active ingredient selected from among:
  (a) a peptide of the present invention;
  (b) a polynucleotide encoding such a peptide of the present invention in an expressible form;
  (c) an APC presenting a peptide of the present invention on its surface;
  (d) an exosome presenting a peptide of the present invention on its surface; and
  (e) a CTL of the present invention.

According to the present invention, peptides having an amino acid sequence selected from among SEQ ID NOs: 1, 2, 4, 6, 11, 12, 13, 15, 17, 19, 20, 21, 22, 23, 24, 25 and 27 have been found to be HLA-A24 restricted epitope peptides that can induce potent and specific immune response against cancer expressing HLA-A24 and UBE2T in a subject. Also, peptides having an amino acid sequence selected from among SEQ ID NOs: 29, 30, 32, 36, 38, 41, 48, 49, 51, 52, 53, 55, 56 and 58 have been found to be HLA-A2 restricted epitope peptides that can induce potent and specific immune response against cancer expressing HLA-A2 and UBE2T in a subject. Therefore, the pharmaceutical compositions or agents which include any of these peptides with the amino acid sequence selected from among SEQ ID NOs: 1, 2, 4, 6, 11, 12, 13, 15, 17, 19, 20, 21, 22, 23, 24, 25 and 27 are particularly suited for the administration to subjects whose HLA antigen is HLA-A24. On the other hand, the pharmaceutical compositions or agents which include any of these peptides with the amino acid sequence selected from among SEQ ID NOs: 29, 30, 32, 36, 38, 41, 48, 49, 51, 52, 53, 55, 56 and 58 are particularly suited for the administration to subjects whose HLA antigen is HLA-A2. The same applies to pharmaceutical compositions or agents that contain polynucleotides encoding any of these peptides (i.e., the polynucleotides of the present invention).

Cancers to be treated and/or prevented by the pharmaceutical compositions or agents of the present invention are not limited and include all kinds of cancers in which UBE2T is involved, examples of which include, but not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

The pharmaceutical compositions or agents of the present invention can contain in addition to the aforementioned active ingredients, other peptides which have the ability to induce CTLs against cancerous cells, other polynucleotides encoding the other peptides, other cells that present the other peptides, or such. Examples of such "other" peptides that have the ability to induce CTLs against cancerous cells include, but are not limited to peptides derived from cancer specific antigens (e.g., identified TAAs).

If needed, the pharmaceutical compositions or agents of the present invention can optionally include other therapeutic substances as an active ingredient, as long as the substance does not inhibit the antitumoral effect of the active ingredient of the present invention, e.g., any of the peptides, polynucleotides, exosomes, APCs, CTLs of the present invention. For example, formulations can include anti-inflammatory substances, pain killers, chemotherapeutics, and the like. In addition to including other therapeutic substances in the medicament itself, the medicaments of the present invention can also be administered sequentially or concurrently with the one or more other pharmacologic compositions. The amounts of medicament and pharmacologic composition depend, for example, on what type of pharmacologic composition(s) is/are used, the disease being treated, and the scheduling and routes of administration.

It should be understood that in addition to the ingredients particularly mentioned herein, the pharmaceutical compositions or agent of the present invention can include other substances conventional in the art having regard to the type of formulation in question.

In one embodiment of the present invention, the pharmaceutical compositions or agents of the present invention can be packaged in articles of manufacture and kits containing materials useful for treating the pathological conditions of the disease to be treated, e.g., cancer. The article of manufacture can include a container of any of the present pharmaceutical compositions or agents with a label. Suitable containers include bottles, vials, and test tubes. The containers can be formed from a variety of materials, such as glass or plastic. The label on the container should indicate the composition or agent is used for treating or prevention of one or more conditions of the disease. The label can also indicate directions for administration and so on.

In addition to the container described above, a kit including a pharmaceutical composition or agent of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical compositions or agents of the present invention can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Compositions Containing the Peptides as Active Ingredients

The peptide of the present invention can be administered directly as a pharmaceutical composition or agent, or if necessary, may be formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical compositions or agents of the present invention can contain as necessary, stabilizers, suspensions, preservatives, surfactants and such. The pharmaceutical compositions or agents of the present invention can be used for anti-cancer purposes.

The peptides of the present invention can be prepared in combination, which includes two or more of peptides of the present invention, to induce CTLs in vivo. The peptides can be in a cocktail or can be conjugated to each other using standard techniques. For example, the peptides can be chemically linked or expressed as a single fusion polypeptide. The peptides in the combination can be the same or different. By administering the peptides of the present invention, the peptides are presented in high density by the HLA antigens on APCs, and then CTLs that specifically react toward the complex formed between the displayed peptide and the HLA antigen are induced. Alternatively, APCs (e.g., DCs) may be removed from a subject and then stimulated by the peptides of the present invention to obtain APCs that present any of the peptides of the present invention on their cell surface. These APCs can be re-administered to the subject to induce CTLs in the subject, and as a result, aggressiveness towards the tumor-associated endothelium can be increased.

The pharmaceutical compositions or agents for the treatment and/or prevention of cancer that include any of peptides of the present invention as active ingredients can also include an adjuvant so that cellular immunity will be established effectively. Alternatively, the pharmaceutical compositions or agents of the present invention can be administered with other active ingredients, or can be administered by formulation into granules. An adjuvant refers to any compound, substance or composition that enhances the immune response against a protein when administered together (or successively) with the protein having immunological activity. Adjuvants contemplated herein include those described in the literature (Johnson A G, Clin Microbiol Rev 1994, 7: 277-89). Examples of suitable adjuvants include, but are not limited to, aluminum phosphate, aluminum hydroxide, alum, cholera toxin, salmonella toxin, IFA (Incomplete Freund's adjuvant), CFA (Complete Freund's adjuvant), ISCOMatrix, GM-CSF, CpG, O/W emulsion and the like.

Furthermore, liposome formulations, granular formulations in which the peptide is bound to few-micrometers diameter beads, and formulations in which a lipid is bound to the peptide may be conveniently used.

In another embodiment, the peptides of the present invention may also be administered in the form of a pharmaceutically acceptable salt. Examples of preferred salts include, but are not limited to, salts with an alkali metal, salts with a metal, salts with an organic base, salts with an amine, salts with an organic acid (acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (hydrochloric acid, phosphoric acid, hydrobromic acid, sulfuric acid, nitric acid, and so on). As used herein, the phrase "pharmaceutically acceptable salt" refers to those salts which retain the biological effectiveness and properties of the compound and which are obtained by reaction with inorganic or organic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical compositions or agents of the present invention may further include a component that primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As other examples of lipids, E. coli lipoproteins, such as tripalmitoyl-S-glyceryl-cysteinyl-seryl-serine (P3CSS) can be used to prime CTLs when covalently attached to an appropriate peptide (see, e.g., Deres et al., Nature 1989, 342: 561-4).

Examples of suitable methods of administration, include, but are not necessarily limited to, oral, and intradermal, subcutaneous, intramuscular, intraosseous, peritoneal and intravenous injection, or such, and systemic administration or local administration to the vicinity of the targeted sites. The administration can be performed by single administration or boosted by multiple administrations. A pharmaceutically or therapeutically effective amount of the peptide of the present invention can be administered to a subject in need of treatment of cancer expressing UBE2T. Alternatively, an amount of the peptide of the present invention sufficient to enhance or stimulate immunological response mediated with CTLs, and/or to induce CTLs against cancer or tumor expressing UBE2T can be administered to a subject carrying a cancer expressing UBE2T. The dose of the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 30 mg, for example, 0.1 mg to 10 mg, for example, 0.5 mg to 5 mg, and can be administered once in a few days to a few months, for example, once a week. One skilled in the art can appropriately select a suitable dose.

(2) Pharmaceutical Compositions Containing Polynucleotides as Active Ingredients The pharmaceutical compositions or agents of the present invention can also contain nucleic acids encoding the peptide(s) of the present invention in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736, 524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan R C, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al. in Current Protocols in Molecular Biology (John Wiley & Sons, NY, 1993); and Krieger in Gene Transfer and Expression, A Laboratory Manual (Stockton Press, NY, 1990).

Administration can be performed by oral, or intradermal, subcutaneous, intravenous, intramuscular, intraosseous, or peritoneal injection, or such, and systemic administration or local administration to the vicinity of the targeted sites finds use. The administration can be performed by single administration or boosted by multiple administrations. A pharmaceutically or therapeutically effective amount of the polynucleotide can be administered to a subject in need of treatment of cancer expressing UBE2T. Alternatively, an amount of the polynucleotide of the present invention sufficient to enhance or stimulate immunological response mediated with CTLs, and/or to induce CTLs against cancer or tumor expressing UBE2T can be administered to a subject carrying a cancer expressing UBE2T. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 30 mg, for example, 0.1 mg to 10 mg, for example, 0.5 mg to 5 mg, and can be administered once every a few days to once every few months, for example, once a week. One skilled in the art can appropriately select the suitable dose.

X. Methods of Using the Peptides, Polynucleotide, Exosomes, APCs and CTLs

The peptides and polynucleotides of the present invention can be used for preparing or inducing APCs and CTLs. The exosomes and APCs of the present invention can be also used for preparing or inducing CTLs. The peptides, polynucleotides, exosomes and APCs can be used in combination with any other compounds as long as the additional compounds do not inhibit their CTL inducibility. Thus, any of the aforementioned pharmaceutical compositions or agents of the present invention can be used for preparing or inducing CTLs. In addition thereto, those including the peptides or polynucleotides can be also used for preparing or inducing APCs as explained below.

(1) Methods of Inducing Antigen-Presenting Cells (APCs)

The present invention provides methods of inducing APCs with CTL inducibility using the peptides or polynucleotides of the present invention.

The methods of the present invention include the step of contacting APCs with the peptides of the present invention in vitro, ex vivo or in vivo. For example, the method of contacting an APC with the peptide ex vivo can include steps of:

a: collecting APCs from a subject, and
b: contacting the APCs of step a with the peptide of the present invention.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any one of peptides of the present invention can be used by itself or in combination with one or more of other peptides of the present invention and/or one or more of CTL-inducible peptides derived from TAAs other than UBE2T.

On the other hand, when the peptides of the present invention are administered to a subject, APCs are contacted with the peptides in vivo, and consequently, APCs with CTL inducibility are induced in the body of the subject. Thus, the method of the present invention may include administering the peptide of the present invention to a subject to induce an APC with CTL inducibility in the body of the subject. Similarly, when the polynucleotide of the present invention is administered to a subject in an expressible form, the peptide of the present invention is expressed and contacted with APCs in vivo, and consequently, APCs with CTL inducibility are induced in the body of the subject. Thus, the present invention may also include administering the polynucleotide of the present invention to a subject to induce an APC with CTL inducibility in the body of the subject. The phrase "expressible form" is described above in section "IX. Pharmaceutical Agents or Compositions (2) Pharmaceutical Agents or Compositions Containing Polynucleotides as Active Ingredients".

Furthermore, the method of the present invention may include introducing the polynucleotide of the present invention into an APC to induce an APC with CTL inducibility. For example, the method can include steps of:

a: collecting APCs from a subject, and
b: introducing a polynucleotide encoding the peptide of the present invention into the APC collected in step a.

Step b can be performed as described above in section "VI. Antigen-Presenting Cells".

Alternatively, the present invention provides a method for preparing an antigen-presenting cell (APC) which can specifically induce CTL activity against UBE2T, wherein the method can include one of the following steps:

(a) contacting an APC with a peptide of the present invention in vitro, ex vivo or in vivo; and
(b) introducing a polynucleotide encoding a peptide of the present invention into an APC.

Alternatively, the present invention provides methods for inducing an APC having CTL inducibility, wherein the methods include the step selected from among:

(a) contacting an APC with the peptide of the present invention; and
(b) introducing the polynucleotide encoding the peptide of the present invention into an APC.

In a preferred embodiment, the present invention provides the method of inducing or preparing an APC having CTL inducibility, such method including one of the following steps:

(a) contacting an APC expressing HLA-A24 with a peptide having an amino acid sequence selected from among SEQ ID NOs: 1, 2, 4, 6, 11, 12, 13, 15, 17, 19, 20, 21, 22, 23, 24, 25 and 27 or modified peptide thereof in vitro, ex vivo or in vivo; and
(b) introducing a polynucleotide encoding a peptide having an amino acid sequence selected from among SEQ ID NOs: 1, 2, 4, 6, 11, 12, 13, 15, 17, 19, 20, 21, 22, 23, 24, 25 and 27 or modified peptide thereof into an APC expressing HLA-A24.

APCs induced by the above method present such peptides via HLA-A24 on their surface, and can induce CTLs having specific cytotoxic activity against cells expressing HLA-A24 and UBE2T.

In another embodiment, the present invention provides the method of inducing or preparing an APC having CTL inducibility, such method including one of the following steps:

(a) contacting an APC expressing HLA-A2 with a peptide having an amino acid sequence selected from among SEQ ID NOs: 29, 30, 32, 36, 38, 41, 48, 49, 51, 52, 53, 55, 56 and 58 or modified peptide thereof in vitro, ex vivo or in vivo; and
(b) introducing a polynucleotide encoding a peptide having an amino acid sequence selected from among SEQ ID NOs: 29, 30, 32, 36, 38, 41, 48, 49, 51, 52, 53, 55, 56 and 58 or modified peptide thereof into an APC expressing HLA-A2.

APCs induced by the above method present such peptides via HLA-A2 on their surface, and can induce CTLs having specific cytotoxic activity against cells expressing HLA-A2 and UBE2T.

The methods of the present invention can be carried out in vitro, ex vivo or in vivo. Preferably, the methods of the present invention can be carried out in vitro or ex vivo. APCs used for induction of APCs having CTL inducibility can be preferably APCs expressing HLA-A24 or HLA-A2 antigen. Such APCs can be prepared by the methods well-known in the arts from peripheral blood mononuclear cells (PBMCs) obtained from a subject whose HLA antigen is HLA-A24 or HLA-A2. The APCs induced by the method of the present invention can be APCs that present a complex of the peptide of the present invention and HLA antigen (HLA-A24 or HLA-A2 antigen) in its surface. When APCs induced by the method of the present invention are administered to a subject in order to induce immune responses against cancer in the subject, the subject is preferably the same one from whom APCs are derived. However, the subject may be a different one from the APC donor as long as the subject has the same HLA type with the APC donor.

In another embodiment, the present invention provides agents or compositions for use in inducing an APC having CTL inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having CTL inducibility.

(2) Method of Inducing CTLs

The present invention also provides methods for inducing CTLs using the peptides, polynucleotides, or exosomes or APCs of the present invention.

The present invention also provides methods for inducing CTLs using a polynucleotide encoding both of TCR subunits or polynucleotides encoding each of TCR subunits, wherein the TCR formed by such subunits can recognize (bind to) a complex of the peptide of the present invention and an HLA antigen on a cell surface. Preferably, the methods for inducing CTLs may include at least one step selected from among:

a: contacting a CD8 positive T cell with an antigen-presenting cell that presents on its surface a complex of an HLA antigen and a peptide of the preset invention b: contacting a CD8 positive T cell with an exosome that presents on its surface a complex of an HLA antigen and a peptide of the preset invention; and c: introducing a polynucleotide encoding both of TCR subunits or polynucleotides encoding each of TCR subunits into a CD8 positive T cell, wherein the TCR formed by such subunits can recognize (bind to) a complex of a peptide of the present invention and an HLA antigen on a cell surface.

When the peptides, polynucleotides, APCs, or exosomes of the present invention are administered to a subject, CTLs are induced in the body of the subject, and the strength of immune responses targeting cancer cells expressing UBE2T is enhanced. Thus, the methods of the present invention can include the step of administering the peptides, polynucleotides, APCs or exosomes of the present invention to a subject.

Alternatively, CTLs can be also induced by using them ex vivo or in vitro, and after inducing CTLs, the activated CTLs can be returned to the subject. For example, the method can include steps of:

a: collecting APCs from subject, b: contacting the APCs of step a, with the peptide of the present invention, and c: co-culturing the APCs of step b with CD8 positive T cells.

The APC to be co-cultured with the CD8 positive T cell in above step c can also be prepared by transferring a polynucleotide of the present invention into an APC as described above in section "VI. Antigen-Presenting Cells", although the present invention is not limited thereto and thus encompasses any APCs that effectively present on its surface a complex of an HLA antigen and a peptide of the present invention.

One may optionally utilize exosomes that present on its surface a complex of an HLA antigen and the peptide of the present invention instead of the aforementioned APCs. Namely, the present invention can includes the step of co-culturing exosomes presenting on its surface a complex of an HLA antigen and the peptide of the present invention and CD8 positive T cells. Such exosomes can be prepared by the methods described above in section "V. Exosomes". Suitable APCs and exosomes for the method of the present invention present a complex of the peptide of the present invention and HLA-A24 or HLA-A2 on its surface.

For example, an APC or exosome that present a complex of an HLA-A24 and a peptide having an amino acid sequence selected from among SEQ ID NOs: 1, 2, 4, 6, 11, 12, 13, 15, 17, 19, 20, 21, 22, 23, 24, 25 and 27 (or modified peptide thereof) on its surface can be preferably utilize for inducing a CTL having specific cytotoxic activity against a cell expressing HLA-A24 and UBE2T. Likewise, an APC or exosome that present a complex of an HLA-A2 and a peptide having an amino acid sequence selected from among SEQ ID NOs: 29, 30, 32, 36, 38, 41, 48, 49, 51, 52, 53, 55, 56 and 58 (or modified peptide thereof) on its surface can be preferably utilize for inducing a CTL having specific cytotoxic activity against a cell expressing HLA-A2 and UBE2T.

Furthermore, the CTL can be induced by introducing a polynucleotide encoding both of the TCR subunits or polynucleotides encoding each of the TCR subunits into CD8 positive T cell, wherein the TCR formed by such subunits can bind to a complex of the peptide of the present invention and an HLA antigen on a cell surface. Such transduction can be performed as described above in section "VIII. T Cell Receptor (TCR)".

The methods of the present invention can be carried out in vitro, ex vivo or in vivo. Preferably, the methods of the present invention can be carried out in vitro or ex vivo. CD8 positive T cells used for induction of CTLs can be prepared by well-known methods in the art from PBMCs obtained from a subject. In preferred embodiments, the donor for CD8 positive T cells can be a subject whose HLA antigen is HLA-A24 or HLA-A2. The CTLs induced by the methods of the present invention can be CTLs that can recognize cells presenting a complex of the peptide of the present invention and an HLA antigen on its surface. Such CTLs can show specific cytotoxic activity against cells that present the peptide of the present invention on its surface, and therefore, can show specific cytotoxic activity against cells expressing UBE2T (e.g., cancer cells). When CTLs induced by the method of the present invention are administered to a subject in order to induce immune responses against cancer in the subject, the subject is preferably the same one from whom CD8 positive T cells are derived. However, the subject may be a different one from the CD8 positive T cell donor as long as the subject has the same HLA type with the CD8 positive T cell donor.

In addition, the present invention provides a method or process for manufacturing a pharmaceutical composition or agent for inducing a CTL, wherein the method or process includes the step of admixing or formulating the peptide of the present invention with a pharmaceutically acceptable carrier.

In another embodiment, the present invention provides an agent or composition for inducing a CTL, wherein the agent or composition comprises one or more peptide(s), one or more polynucleotide(s), one or more APCs, and/or one or more exosomes of the present invention.

In another embodiment, the present invention provides the use of the peptide, polynucleotide, APC or exosome of the present invention in the manufacture of an agent or composition formulated for inducing a CTL.

Alternatively, the present invention further provides the peptide, polynucleotide, APC or exosome of the present invention for use in inducing a CTL.

XI. Methods of Inducing Immune Response

Moreover, the present invention provides methods of inducing immune responses against diseases related to UBE2T. Suitable diseases include cancer, examples of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

The methods of the present invention may include the step of administering an agent or composition containing any of the peptides of the present invention or polynucleotides encoding them. The inventive methods also contemplate the administration of exosomes or APCs presenting any of the peptides of the present invention. For details, see the item of "IX. Pharmaceutical Agents or Compositions", particularly the part describing the use of the pharmaceutical compositions of the present invention as vaccines. In addition, the exosomes and APCs that can be employed for the present methods for inducing immune response are described in detail under the items of "V. Exosomes", "VI. Antigen-Presenting Cells (APCs)", and (1) and (2) of "X. Methods Using the Peptides, Exosomes, APCs and CTLs", supra.

The present invention also provides a method or process for manufacturing a pharmaceutical composition or agent for inducing immune response against cancer, wherein the method may include the step of admixing or formulating the peptide of the present invention with a pharmaceutically acceptable carrier.

Alternatively, the method of the present invention may include the step of administrating a vaccine or a pharmaceutical composition or agent of the present invention that contains:

(a) a peptide of the present invention;
(b) a polynucleotide encoding the peptide of the present invention in an expressible form;
(c) an APC presenting the peptide of the present invention on its surface;
(d) an exosome presenting the peptide of the present invention on its surface; or
(e) a CTL of the present invention.

In the context of the present invention, a cancer over-expressing UBE2T can be treated with these active ingredients. Examples of such cancer include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor. Accordingly, prior to the administration of the vaccines or pharmaceutical compositions or agent including any of aforementioned active ingredients, it is preferable to confirm whether the expression level of UBE2T in cancerous cells or tissues collected from the subject to be treated is elevated as compared with normal cells or tissues collected from the same subject. Thus, in one embodiment, the present invention provides a method for treating cancer (over)expressing UBE2T in a patient in need thereof, such method including the steps of:

i) determining the expression level of UBE2T in a biological sample obtained from a subject with the cancer to be treated;
ii) comparing the expression level of UBE2T with normal control; and
iii) administrating at least one component selected from among (a) to (e) described above to a subject with cancer over-expressing UBE2T compared with normal control.

Alternatively, the present invention provides a vaccine or pharmaceutical composition including at least one component selected from among (a) to (e) described above, to be administered to a subject having cancer over-expressing UBE2T. In other words, the present invention further provides a method for identifying a subject to be treated with the peptide of the present invention, such method including the step of determining an expression level of UBE2T in a subject-derived biological sample, wherein an increase of the expression level as compared to a normal control level of the gene indicates that the subject may have cancer which may be treated with the peptide of the present invention.

Further, in preferred embodiments, the HLA type of a subject may be identified before administering the peptides of the present invention. For example, peptides having the amino acid sequence of SEQ ID NO: 1, 2, 4, 6, 11, 12, 13, 15, 17, 19, 20, 21, 22, 23, 24, 25, or 27 are preferably administered to a subject identified as having HLA-A24. Alternatively, peptides having the amino acid sequence of SEQ ID NO: 29, 30, 32, 36, 38, 41, 48, 49, 51, 52, 53, 55, 56 or 58 are preferably administered to a subject identified as having HLA-A2.

Any subject-derived cell or tissue can be used for the determination of the expression level of UBE2T as long as it can include the transcription or translation product of UBE2T. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from cancerous tissue. Further, if necessary, the cell may be purified from the obtained bodily tissues and fluids, and then used as the subjected-derived sample.

According to the present invention, the expression level of UBE2T in a biological sample obtained from a subject may be determined. The expression level of UBE2T can be determined at the transcription (nucleic acid) product level, using methods known in the art. For example, the mRNA of UBE2T may be quantified using probes by hybridization methods (e.g., Northern hybridization). The detection may be carried out on a chip or an array. The use of an array is preferable for detecting the expression level of UBE2T. Those skilled in the art can prepare such probes utilizing the sequence information of UBE2T. For example, the cDNA of UBE2T may be used as the probes. If necessary, the probes may be labeled with a suitable label, such as dyes, fluorescent substances and isotopes, and the expression level of UBE2T may be detected as the intensity of the hybridized labels.

Furthermore, the transcription product of UBE2T may be quantified using primers by amplification-based detection methods (e.g., RT-PCR). Such primers may be prepared based on the available sequence information of UBE2T.

Specifically, a probe or primer used for the present method hybridizes under stringent, moderately stringent, or low stringent conditions to the mRNA of UBE2T. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0

M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including a UBE2T sequence, or an anti-sense strand nucleotide sequence of a nucleic acid including a UBE2T sequence, or of a naturally occurring mutant of these sequences. In particular, for example, in a preferred embodiment, an oligonucleotide having 5-50 in length can be used as a primer for amplifying the genes, to be detected. More preferably, mRNA or cDNA of a UBE2T gene can be detected with oligonucleotide probe or primer of a specific size, generally 15-30 bases in length. The size may range from at least 10 nucleotides, at least 12 nucleotides, at least 15 nucleotides, at least 20 nucleotides, at least 25 nucleotides, at least 30 nucleotides and the probes and primers may range in size from 5-10 nucleotides, 10-15 nucleotides, 15-20 nucleotides, 20-25 nucleotides and 25-30 nucleotides. In preferred embodiments, length of the oligonucleotide probe or primer can be selected from 15-25 nucleotides. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product of UBE2T may be detected for the identification of a subject to be treated by the method of the present invention. For example, the quantity of UBE2T protein (SEQ ID NO: 65) may be determined. Examples of methods for determining the quantity of the UBE2T protein as the translation product include immunoassay methods using an antibody specifically recognizing the UBE2T protein. The antibody may be monoclonal or polyclonal. Furthermore, any fragment or modification (e.g., chimeric antibody, scFv, Fab, F(ab')$_2$, Fv, etc.) of the antibody may be used for the detection, as long as the fragment or modified antibody retains the binding ability to the UBE2T protein. Methods to prepare these kinds of antibodies are well known in the art, and any method may be employed to prepare such antibodies and equivalents thereof.

As another method to detect the expression level of UBE2T based on its translation product, the intensity of staining may be measured via immunohistochemical analysis using an antibody against the UBE2T protein. Namely, in this measurement, strong staining indicates increased presence/level of the UBE2T protein and, at the same time, high expression level of UBE2T.

The expression level of the UBE2T gene in a subject-derived sample can be determined to be increased if the expression level increases from the control level (e.g., the expression level in normal cells) of the UBE2T by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells by using a sample(s) previously collected and stored from a healthy subject/subjects. In addition, normal cells obtained from non-cancerous regions of an organ that has the cancer to be treated may be used as normal control. Alternatively, the control level may be determined by a statistical method based on the results obtained by analyzing previously determined expression level(s) of UBE2T in samples from subjects whose disease states are known. Furthermore, the control level can be derived from a database of expression patterns from previously tested cells. Moreover, according to an aspect of the present invention, the expression level of UBE2T in a biological sample may be compared to multiple control levels, which are determined from multiple reference samples. It is preferred to use a control level determined from a reference sample derived from a tissue type similar to that of the subject-derived biological sample. Moreover, it is preferred to use the standard value of the expression levels of UBE2T gene in a population with a known disease state. The standard value may be obtained by any method known in the art. For example, a range of mean+/−2 S.D. or mean+/−3 S.D. may be used as the standard value.

Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of UBE2T is increased as compared to the normal control level, the subject may be identified as a subject with cancer to be treated by administration of the pharmaceutical composition or agent of the present invention.

The present invention also provides a method of selecting a subject for cancer treatment using aforementioned pharmaceutical compositions or agents of the present invention, such method including the steps of:

a) determining the expression level of UBE2T in biological sample(s) obtained from a subject with cancer;

b) comparing the expression level of UBE2T determined in step a) with a normal control level; and c) selecting the subject for cancer treatment by the pharmaceutical compositions or agents of the present invention, if the expression level of UBE2T is increased as compared to the normal control level.

In some embodiments, such a method may further comprise the step of identifying, after or before the steps a)-c) defined above, a subject having an HLA selected from the group consisting of HLA-A24 and HLA-A2. Cancer therapy according to the present invention is preferable for a subject that suffers from cancer overexpressing UBE2T and has HLA-A24 or HLA-A2. Methods for HLA typing are well known in the art. For example, PCR-based methods for typing HLA alleles are well known. Antibodies specific for each HLA molecule are also appropriate tools for identifying HLA types of a subject.

In one embodiment, the present invention further provides a diagnostic kit including one or more peptide of the present invention.

Cancer can be diagnosed by detecting antibodies against the peptide of the present invention in a subject-derived sample (e.g., blood) using the peptide of the present invention.

The subject is suspected to be suffering from cancer, if a subject-derived sample (e.g., blood sample) contains antibodies against the peptide of the present invention and the quantity of the antibodies is determined to be more than the cut off value as compared to control level.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceutical composition or agent including the peptide of the present invention as an active ingredient, or the assessment of the treatment effect of the pharmaceutical composition or agent.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from a subject suspected to be suffering from cancer.

The present invention further provides methods and diagnostic agents for evaluating immunological response of subject by using the peptide of the present invention. In one embodiment of the invention, the peptides of the present invention are used as reagents for evaluating or predicting an immune response of a subject. The immune response to be evaluated is induced by contacting an immunogen (i.e., the peptide of the present invention) with immunocompetent cells in vitro or in vivo. In preferred embodiments, the immunocompetent cells for evaluating an immunological response, may be selected from among peripheral blood, peripheral blood lymphocyte (PBL), and peripheral blood mononuclear cell (PBMC). Assay systems that are used for such an analysis include relatively recent technical developments such as tetramer staining assays, staining for intracellular lymphokine and interferon release assays, or ELISPOT assays. In a preferred embodiment, immunocompetent cells to be contacted with the peptide reagent may be antigen presenting cells including dendritic cells.

For example, the peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen-specific cells. The cells can then be identified, for example, by flow cytometry. Such an analysis may be used for diagnostic or prognostic purposes. Cells identified by the procedure can also be used for therapeutic purposes.

The peptides of the present invention may be also used to make antibodies, using techniques well known in the art (see, e.g., CURRENT PROTOCOLS IMMUNOLOGY, Wiley/Greene, NY; and Antibodies A Laboratory Manual, Harlow and Lane, Cold Spring Harbor Laboratory Press, 1989), which may be useful as reagents to diagnose or monitor cancer. Such antibodies may include those that recognize a peptide in the context of an HLA molecule, i. e., antibodies that bind to a peptide-MHC complex.

The peptides and compositions of the present invention have a number of additional uses, some of which are described herein. For instance, the present invention provides a method for diagnosing or detecting a disorder characterized by expression of a UBE2T polypeptide.

For example, the diagnosis can be done, by a method which allows direct quantification of antigen-specific T cells by staining with Fluorescein-labelled HLA multimeric complexes (for example, Altman, J. D. et al., 1996, Science 274: 94; Altman, J. D. et al., 1993, Proc. Natl. Acad. Sci. USA 90: 10330;). Staining for intracellular lymphokines, and interferon-gamma release assays or ELISPOT assays also has been provided. Tetramer staining, intracellular lymphokine staining and ELISPOT assays all appear to be at least 10-fold more sensitive than more conventional assays (Murali-Krishna K. et al., 1998, Immunity 8: 177; Lalvani A. et al., 1997, J. Exp. Med. 186: 859; Dunbar P. R. et al., 1998, Curr. Biol. 8: 413;). Pentamers (e.g., US 2004-209295A), dextramers (e.g., WO 02/072631), and streptamers (e.g., Nature medicine 6. 631-637 (2002)) may also be used.

For instance, in some embodiments, the present invention provides a method for diagnosing or evaluating an immunological response of a subject administered at least one of UBE2T peptides of the present invention, the method including the steps of:

(a) contacting an immunogen with immunocompetent cells under the condition suitable for induction of CTL specific to the immunogen;

(b) detecting or determining induction level of the CTL induced in step (a); and (c) correlating the immunological response of the subject with the CTL induction level.

In the present invention, the immunogen is at least one of UBE2T peptides having the amino acid sequences of SEQ ID NO: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 or 58, and peptides having in which such amino acid sequences have been modified with 1, 2 or more amino acid substitution(s). In the meantime, conditions suitable of induction of immunogen specific CTLs are well known in the art. For example, immunocompetent cells may be cultured in vitro under the presence of immunogen(s) to induce immunogen specific CTLs. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTLs as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any UBE2T peptides (e.g., random amino acid sequence).

XII. Antibodies

The present invention further provides antibodies that bind to peptides of the present invention. Preferred antibodies specifically bind to peptides of the present invention and will not bind (or will bind weakly) to those other than the peptides of the present invention.

Antibodies against the peptides of the present invention can find use in cancer diagnostic and prognostic assays. Similarly, such antibodies can find use in the treatment, diagnosis, and/or prognosis of cancers, to the extent UBE2T is also expressed or over-expressed in cancer. Moreover, intracellularly expressed antibodies (e.g., single chain antibodies) may therapeutically find use in treating cancers in which the expression of UBE2T is involved, example of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

The present invention also provides various immunological assays for the detection and/or quantification of the UBE2T protein (SEQ TD NO: 65) or fragments thereof, including peptides consisting of the amino acid sequence selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58. In the context of the present invention, antibodies binding to UBE2T polypeptide preferably recognize the peptide consisting of the amino acid sequence selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58. A binding specificity of an antibody can be confirmed with inhibition test. That is, when the binding between an antibody to be analyzed and full-length of UBE2T polypeptide is inhibited under the presence of any fragment consisting of the amino acid sequence of SEQ ID NO: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 or 58, it is shown that this antibody specifically binds to the fragment. In the context of the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays may include T cell immunogenicity assays (inhibitory or stimulatory) as well as MHC binding assays. In addition, the present invention contemplates immunological imaging methods capable of detecting cancers expressing UBE2T, example of which include, but are not limited to, radioscintigraphic imaging methods using labeled antibodies of the present invention. Such assays find clinical use in the detection, monitoring, and prognosis of UBE2T expressing cancers, examples of which include, but are not limited to, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

The antibody of the present invention can be used in any form, for example as a monoclonal or polyclonal antibody, and may further include anti-serum obtained by immunizing an animal such as a rabbit with the peptide of the present invention, all classes of polyclonal and monoclonal antibodies, human antibodies and humanized antibodies produced by genetic recombination.

The antibody of the present invention can recognize peptides having an amino acid sequence selected from the group consisting of SEQ ID NOs: 1, 2, 4, 6, 11, 12, 13, 15, 17, 19, 20, 21, 22, 23, 24, 25, 27, 29, 30, 32, 36, 38, 41, 48, 49, 51, 52, 53, 55, 56 and 58. Methods for synthesizing oligopeptide are well known in the arts. After the synthesis, peptides may be optionally purified prior to use as immunogen. In the context of the present invention, the oligopeptide (e.g., 9 or 10 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the present invention may be inserted into a known expression vector, which is then used to transform a host cell as described herein. The desired peptide may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primates may be used. Animals of the family Rodentia include, for example, mouse, rat and hamster. Animals of the family Lagomorpha include, for example, rabbit. Animals of the Primate family include, for example, a monkey of Catarrhini (old world monkey) such as Macaca fascicularis, rhesus monkey, sacred baboon and chimpanzees.

Methods for immunizing animals with antigens are known in the art. Intraperitoneal injection or subcutaneous injection of antigens is a standard method for the immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies may include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. S 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Monoclonal antibodies obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, as long as it binds to the peptide of the present invention. For instance, the antibody fragment may be Fab, $F(ab')_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co, et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used includes, for example, Hyper D, POROS and Sepharose F. F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the present invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. BIAcore (Pharmacia) may be used to evaluate the activity of the antibody of the present invention.

XIII. Vectors and Host Cells

The present invention also provides a vector and host cell into which a polynucleotide encoding the peptide of the present invention is introduced. A vector of the present invention may be used to keep a polynucleotide, especially a DNA, of the present invention in host cell, to express a peptide of the present invention, or to administer a polynucleotide of the present invention for gene therapy.

When E. coli is a host cell and the vector is amplified and produced in a large amount in E. coli (e.g., JM109, DH5 alpha, HB101 or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the peptide of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase, for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Mizushima S, et al., Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from Bacillus subtilis (e.g., pPL608, pKTH50) can be used for producing the peptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Although methods and materials similar or equivalent to those described herein can be used in the practice or testing of the present invention, suitable methods and materials are described. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Experimental 1

Materials and Methods
Cell Lines
TISI, HLA-A*2402-positive B-lymphoblastoid cell line, was purchased from the IHWG Cell and Gene Bank (Seattle, Wash.). T2, HLA-A*0201-positive B-lymphoblastoid cell line, and COS7, African green monkey kidney cell line, was purchased from ATCC.

Candidate selection of peptides derived from UBE2T
9-mer and 10-mer peptides derived from UBE2T that bind to HLA-A*2402 or HLA-A*0201 molecule were predicted using "NetMHC3.2" binding prediction server ((Internet at cbs.dtu.dk/services/NetMHC/) (Buus et al., Tissue Antigens. 2003 November, 62(5):378-84; Nielsen et al., Protein Sci. 2003 May, 12(5):1007-17, Bioinformatics. 2004 Jun. 12; 20(9):1388-97) and "BIMAS" (Internet at bimas.cit.nih.gov/molbio/hla_bind), Parker et al., J Immunol 1994, 152(1): 163-75, Kuzushima et al., Blood 2001, 98(6): 1872-81). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide at 20 mg/ml and stored at −80 degrees C.

In Vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003, 63(14): 4112-8). Specifically, peripheral blood mononuclear cells isolated from a normal volunteer (HLA-A*2402 or HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiation (20 Gy) and mixing at a 1:20 ratio with autologous CD8$^+$ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8$^+$ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTLs were tested against peptide-pulsed TISI cells or peptide-pulsed TS cells after the 3rd round of peptide stimulation on day 21 (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Expansion Procedure

CTLs were expanded in culture using the method similar to the one described by Riddell et al. (Walter E A et al., N Engl J Med 1995 333(16): 1038-44; Riddell S R et al., Nat Med 1996, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed TISI cells or peptide-pulsed T2 cells ($1 \times 10^4$/well) were prepared as stimulator cells. Cultured cells in 48 wells were used as responder cells. IFN-gamma ELISPOT assay and IFN-gamma ELISA assay were performed according to manufacture's procedure.

Establishment of the Cells Forcibly Expressing Either or Both of the Target Gene and HLA-A24 or HLA-A2

The cDNA encoding an open reading frame of UBE2T, HLA-A*2402 or HLA-A*0201 was amplified by PCR. The PCR-amplified product was cloned into an expression vector. The vectors were transfected into COST cells, which are UBE2T-null, HLA-A*2402-null and HLA-A*0201-null cell line, using lipofectamine 2000 (Invitrogen) according to the manufacturer's recommended procedures. After 2 days from transfection, the transfected cells were harvested with versene (Invitrogen) and used as the target cells ($5 \times 10^4$ cells/well) for CTL activity assay.

Results

Enhanced UBE2T Expression in Cancers

The wide gene expression profile data obtained from various cancers using cDNA-microarray revealed that UBE2T (GenBank Accession No. NM 014176 (SEQ ID No: 64)) expression was elevated. UBE2T expression was validly elevated in 24 out of 24 bladder cancers, 44 out of 50 breast cancers, 14 out of 15 cervical cancers, 12 out of 12 cholangiocellular carcinomas, 9 out of 16 CMLs, 9 out of 9 colorectal cancers, 31 out of 47 esophageal cancers, 5 out of 8 gastric cancers, 2 out of 2 diffuse-type gastric cancers, 23 out of 27 NSCLCs, 3 out of 3 lymphomas, 9 out of 16 osteosarcomas, 3 out of 7 ovarian cancers, 3 out of 3 pancreatic cancers, 21 out of 23 prostate cancers, 12 out of 12 SCLCs, 11 out of 26 soft tissue tumors and 7 out of 9 testicular tumors, as compared with corresponding normal tissues (Table 1).

TABLE 1

Ratio of cases observed up-regulation of UBE2T in cancerous tissues as compared with normal corresponding tissues.

| Cancer/Tumor | Ratio |
| --- | --- |
| Bladder cancer | 24/24 |
| Breast cancer | 44/50 |
| Cervical cancer | 14/15 |
| Cholangiocellular carcinoma | 12/12 |
| CML | 9/16 |
| Colorectal cancer | 9/9 |
| Esophageal cancer | 31/47 |
| Gastric cancer | 5/8 |
| Diffuse-type gastric cancer | 2/2 |
| NSCLC | 23/27 |
| Lymphoma | 3/3 |
| Osteosarcoma | 9/16 |
| Ovarian cancer | 3/7 |
| Pancreatic cancer | 3/3 |

TABLE 1-continued

Ratio of cases observed up-regulation of UBE2T in cancerous tissues as compared with normal corresponding tissues.

| Cancer/Tumor | Ratio |
| --- | --- |
| Prostate cancer | 21/23 |
| SCLC | 12/12 |
| Soft tissue tumor | 11/26 |
| Testicular tumor | 7/9 |

Prediction of HLA-A24 Binding Peptides Derived from UBE2T

Table 2a and 2b show the HLA-A24 binding 9 mer and 10 mer peptides of UBE2T in the order of high binding affinity. A total of 27 peptides with potential HLA-A24 binding ability were selected and examined to determine the epitope peptides.

TABLE 2a

HLA-A24 binding 9 mer peptides derived from UBE2T

| SEQ ID NO | Start Position | amino acid sequence | Kd (nM) |
| --- | --- | --- | --- |
| 1 | 60 | RYPFEPPQI | 25 |
| 2 | 45 | PYEKGVFKL | 752 |
| 3 | 124 | LMADISSEF | 1463 |
| 4 | 133 | KYNKPAFLK | 2283 |
| 5 | 55 | VIIPERYPF | 3082 |
| 6 | 138 | AFLKNARQW | 3317 |
| 7 | 6 | RLKRELHML | 3711 |
| 8 | 71 | LTPIYHPNI | 4077 |
| 9 | 131 | EFKYNKPAF | 4692 |
| 10 | 62 | PFEPPQIRF | 7647 |
| 11 | 43 | NTPYEKGVF | 9498 |
| 12 | 106 | TVLTSIQLL | 9831 |

| SEQ ID NO | Start Position | amino acid sequence | Binding score |
| --- | --- | --- | --- |
| 13 | 3 | RASRLKREL | 10.56 |
| 14 | 84 | RICLDVLKL | 8.8 |
| 15 | 105 | ATVLTSIQL | 6 |
| 16 | 74 | IYHPNIDSA | 6 |

TABLE 2b

HLA-A24 binding 10 mer peptides derived from UBE2T

| SEQ ID NO | Start Position | amino acid sequence | Kd (nM) |
| --- | --- | --- | --- |
| 17 | 130 | SEFKYNKPAF | 776 |
| 18 | 123 | PLMADISSEF | 5392 |
| 19 | 131 | EFKYNKPAFL | 7050 |

TABLE 2b-continued

HLA-A24 binding 10 mer peptides derived from UBE2T

| SEQ ID NO | Start Position | amino acid sequence | Binding score |
| --- | --- | --- | --- |
| 20 | 133 | KYNKPAFLKN | 19.8 |
| 21 | 99 | RPSLNIATVL | 11.2 |
| 22 | 154 | KQKADEEEML | 8 |
| 23 | 105 | ATVLTSIQLL | 7.2 |
| 24 | 115 | MSEPNPDDPL | 7.2 |
| 25 | 177 | STQKRKASQL | 6 |
| 26 | 30 | QMDDLRAQIL | 5.76 |
| 27 | 44 | TPYFKGVFKL | 5.28 |

Start position indicates the number of amino acid residue from the N-terminus of UBE2T.

Binding score and dissociation constant [Kd (nM)] are derived from "BIMAS" and "NetMHC3.2", respectively.

Prediction of HLA-A02 Binding Peptides Derived from UBE2T

Table 3a and 3b show the HLA-A02 binding 9 mer and 10 mer peptides of UBE2T in the order of high binding affinity. A total of 36 peptides with potential HLA-A02 binding ability were selected and examined to determine the epitope peptides.

TABLE 3a

HLA-A02 binding 9 mer peptides derived from UBE2T

| SEQ ID NO | Start Position | amino acid sequence | Kd (nM) |
| --- | --- | --- | --- |
| 28 | 161 | EMLDNLPEA | 76 |
| 29 | 107 | VLTSIQLLM | 385 |
| 30 | 30 | QMDDLRAQI | 473 |
| 31 | 103 | NIATVLTSI | 668 |
| 32 | 106 | TVLTSIQLL | 1048 |
| 33 | 124 | LMADISSEF | 1595 |
| 34 | 6 | RLKRELIIML | 1653 |
| 35 | 101 | SLNIATVLT | 3347 |
| 36 | 49 | GVFKLEVII | 5114 |
| 37 | 70 | FLTPIYHPN | 5950 |
| 38 | 13 | MLATEPPPG | 6039 |
| 39 | 84 | RICLDVLKL | 6284 |
| 40 | 66 | PQIRFLTPI | 6587 |
| 41 | 132 | FKYNKPAFL | 6642 |
| 42 | 96 | GAWRPSLNI | 8188 |
| 43 | 81 | SAGRICLDV | 8938 |

TABLE 3a-continued

HLA-A02 binding 9 mer peptides derived from UBE2T

| | | | |
|---|---|---|---|
| 44 | 14 | LATEPPPGI | 9511 |
| 45 | 105 | ATVLTSIQL | 9872 |

| SEQ ID NO | Start Position | amino acid sequence | Binding score |
|---|---|---|---|
| 46 | 139 | FLKNARQWT | 6.599 |

TABLE 3b

HLA-A02 binding 10 mer peptides derived from UBE2T

| SEQ ID NO | Start Position | amino acid sequence | Kd (nM) |
|---|---|---|---|
| 47 | 13 | MLATEPPPGI | 43 |
| 48 | 70 | FLTPIYHPNI | 49 |
| 49 | 6 | RLKRELHMLA | 1415 |
| 50 | 165 | NLPEAGDSRV | 1902 |
| 51 | 106 | TVLTSIQLLM | 2648 |
| 52 | 102 | LNIATVLTSI | 3011 |
| 53 | 30 | QMDDLRAQIL | 4035 |
| 54 | 17 | HMLATEPPPG | 4153 |
| 55 | 101 | SLNIATVLTS | 4622 |
| 56 | 29 | DQMDDLRAQI | 5029 |
| 57 | 105 | ATVLTSIQLL | 5128 |
| 58 | 38 | ILGGANTPYE | 6464 |
| 59 | 107 | VLTSIQLLMS | 7911 |
| 60 | 161 | EMLDNLPEAG | 9002 |
| 61 | 113 | LLMSEPNPDD | 9132 |
| 62 | 104 | IATVLTSIQL | 9157 |

| SEQ ID NO | Start Position | amino acid sequence | Binding score |
|---|---|---|---|
| 63 | 44 | TPYEKGVFKL | 24.406 |

Start position indicates the number of amino acid residue from the N-terminus of UBE2T.
Binding score and dissociation constant [Kd (nM)] are derived from "BIMAS" and "NetMHC3.2", respectively.

CTL Induction with the Predicted Peptides from UBE2T Restricted with HLA-A *2402

CTLs for those peptides derived from UBE2T were generated according to the protocols as described in "Materials and Methods". Peptide-specific CTL activity was detected by IFN-gamma ELISPOT assay (FIG. 1). It showed that the well number #8 stimulated with UBE2T-A24-9-60 (SEQ ID NO: 1) (a), #1 stimulated with UBE2T-A24-9-45 (SEQ ID NO: 2) (b), #6 stimulated with UBE2T-A24-9-4 (SEQ ID NO: 4) (c), #6 stimulated with UBE2T-A24-9-138 (SEQ ID NO: 6) (d), #4 stimulated with UBE2T-A24-9-43 (SEQ ID NO: 11) (e), #2 stimulated with UBE2T-A24-9-106 (SEQ ID NO: 12) (f), #6 stimulated with UBE2T-A24-9-3 (SEQ ID NO: 13) (g), #3 stimulated with UBE2T-A24-9-105 (SEQ ID NO: 15) (h), #2 stimulated with UBE2T-A24-10-130 (SEQ ID NO: 17) (i), #1 stimulated with UBE2T-A24-10-131 (SEQ ID NO: 19) (j), #3 stimulated with UBE2T-A24-10-133 (SEQ ID NO: 20) (k), #6 stimulated with UBE2T-A24-10-99 (SEQ ID NO: 21) (l), #7 stimulated with UBE2T-A24-10-154 (SEQ ID NO: 22) (m), #8 stimulated with UBE2T-A24-10-105 (SEQ ID NO: 23) (n), #1 stimulated with UBE2T-A24-10-115 (SEQ ID NO: 24) (o), #4 stimulated with UBE2T-A24-10-177 (SEQ ID NO: 25) (p) and #7 stimulated with UBE2T-A24-10-44 (SEQ ID NO: 27) (q) demonstrated potent IFN-gamma production as compared to the control wells. On the other hand, no specific CTL activity was detected by stimulation with other peptides shown in Table 2a and 2b, despite those peptides had possible binding activity with HLA-A*2402. As a typical case of negative data, it was not shown specific IFN-gamma production from the CTL stimulated with UBE2T-A24-9-124 (SEQ ID NO: 3) (r). As a result, it indicated that 17 peptides derived from UBE2T were selected as the peptides that could induce potent CTLs.

CTL Induction with the Predicted Peptides from UBE2T Restricted with HLA-A*0201

CTLs for those peptides derived from UBE2T were generated according to the protocols as described in "Materials and Methods". Peptide-specific CTL activity was detected by IFN-gamma ELISPOT assay (FIG. 2). It showed that the well number #4 stimulated with UBE2T-A02-9-107 (SEQ ID NO: 29) (a), #5 stimulated with UBE2T-A02-9-30 (SEQ ID NO: 30) (b), #7 stimulated with UBE2T-A02-9-106 (SEQ ID NO: 32) (c), #5 stimulated with UBE2T-A02-9-49 (SEQ ID NO: 36) (d), #3 stimulated with UBE2T-A02-9-13 (SEQ ID NO: 38) (e), #4 stimulated with UBE2T-A02-9-132 (SEQ ID NO: 41) (f), #6 stimulated with UBE2T-A02-10-70 (SEQ ID NO: 48) (g), #7 stimulated with UBE2T-A02-10-6 (SEQ ID NO: 49) (h), #8 stimulated with UBE2T-A02-10-106 (SEQ ID NO: 51) (i), #2 stimulated with UBE2T-A02-10-102 (SEQ ID NO: 52) (j), #1 stimulated with UBE2T-A02-10-30 (SEQ ID NO: 53) (k), #8 stimulated with UBE2T-A02-10-101 (SEQ ID NO: 55) (l), #5 stimulated with UBE2T-A02-10-29 (SEQ ID NO: 56) (m) and #3 stimulated with UBE2T-A02-10-38 (SEQ ID NO: 58) (n) demonstrated potent IFN-gamma production as compared to the control wells. On the other hand, no specific CTL activity was detected by stimulation with other peptides shown in Table 3a and 3b, despite those peptides had possible binding activity with HLA-A*0201. As a typical case of negative data, it was not shown specific IFN-gamma production from the CTL stimulated with UBE2T-A02-9-161 (SEQ ID NO: 28) (o). As a result, it indicated that 14 peptides derived from UBE2T were selected as the peptides that could induce potent CTLs.

Establishment of CTL Line and Clone Against UBE2T Derived Peptide

The cells in the well number #8 stimulated with UBE2T-A24-9-60 (SEQ ID NO: 1) (a), #1 stimulated with UBE2T-A24-9-45 (SEQ ID NO: 2) (b), #6 stimulated with UBE2T-A24-9-3 (SEQ ID NO: 13) (c) and #7 stimulated with UBE2T-A24-10-44 (SEQ ID NO: 27), which showed peptide-specific CTL activity in IFN-gamma ELISPOT assay, were expanded and established the CTL lines. CTL activities of these CTL lines were measured by IFN-gamma ELISA (FIG. 3). It demonstrated that the CTL lines showed potent IFN-gamma production against target cells pulsed with the corresponding peptide as compared to target cells without peptide pulse. Furthermore, the CTL clones were established by limiting dilution from the CTL lines as described in "Materials and Methods", and IFN-gamma productions from the CTL clones against TISI cells pulsed with corresponding peptide were measured by IFN-gamma ELISA. Potent IFN-gamma productions were observed from the CTL clones stimulated with UBE2T-A24-9-60 (SEQ ID NO: 1) (a), UBE2T-A24-9-45 (SEQ ID NO: 2) (b) and UBE2T-A24-9-3 (SEQ ID NO: 13) (c) (FIG. 4).

The cells in the well number #4 stimulated with UBE2T-A02-9-107 (SEQ ID NO: 29) (a), #3 stimulated with UBE2T-A02-9-13 (SEQ ID NO: 38) (b), #6 stimulated with UBE2T-A02-10-70 (SEQ ID NO: 48) (c), #2 stimulated with UBE2T-A02-10-102 (SEQ ID NO: 52) (d) and #8 stimulated with UBE2T-A02-10-101 (SEQ ID NO: 55) (e), which showed peptide-specific CTL activity in IFN-gamma ELISPOT assay, were expanded and established the CTL lines. CTL activities of these CTL lines were measured by IFN-gamma ELISA (FIG. 5). It demonstrated that the CTL lines showed potent IFN-gamma production against target cells pulsed with the corresponding peptide as compared to target cells without peptide pulse. Furthermore, the CTL clones were established by limiting dilution from the CTL lines as described in "Materials and Methods", and IFN-gamma productions from the CTL clones against T2 cells pulsed with corresponding peptide were measured by IFN-gamma ELISA. Potent IFN-gamma productions were observed from the CTL clones stimulated with UBE2T-A02-9-107 (SEQ ID NO: 29) (a), UBE2T-A02-9-13 (SEQ ID NO: 38) (b), UBE2T-A02-10-70 (SEQ ID NO: 48) (c), UBE2T-A02-10-102 (SEQ ID NO: 52) (d) and UBE2T-A02-10-101 (SEQ ID NO: 55) (e) (FIG. 6).

Specific CTL Activity Against Target Cells Expressing UBE2T and HLA-A*2402 or HLA-A*0201

The established CTL clone against UBE2T-A24-9-60 (SEQ ID NO: 1) peptide was examined for the ability to recognize target cells that express UBE2T and HLA-A*2402 molecule. COS7 cells transfected with both the full length of UBE2T and HLA-A*2402 gene (a specific model for the target cells that express UBE2T and HLA-A*2402 gene) were prepared as a stimulator cells, and COS7 cells transfected with either full length of UBE2T or HLA-A*2402 were used as the controls. In FIG. 7, the CTL clone stimulated with UBE2T-A24-9-60 (SEQ ID NO: 1) showed potent CTL activity against COS7 cells expressing both UBE2T and HLA-A*2402. On the other hand, no significant specific CTL activity was detected against the controls. Thus, these data clearly demonstrate that UBE2T-A24-9-60 (SEQ ID NO: 1) peptide is endogenously processed and expressed on the target cells with HLA-A*2402 molecule and is recognized by the CTLs. These results indicate that this peptide derived from UBE2T may be available to apply the cancer vaccines for patients with UBE2T expressing tumors.

The established CTL line against UBE2T-A02-10-70 (SEQ ID NO: 48) peptide was examined for the ability to recognize target cells that express UBE2T and HLA-A*0201 molecule. COS7 cells transfected with both the full length of UBE2T and HLA-A*0201 gene (a specific model for the target cells that express UBE2T and HLA-A*0201 gene) were prepared as a stimulator cells, and COS7 cells transfected with either full length of UBE2T or HLA-A*0201 were used as the controls. In FIG. 8, the CTL line stimulated with UBE2T-A02-10-70 (SEQ ID NO: 48) showed potent CTL activity against COS7 cells expressing both UBE2T and HLA-A*0201. On the other hand, no significant specific CTL activity was detected against the controls. Thus, these data clearly demonstrate that UBE2T-A02-10-70 (SEQ ID NO: 48) peptide is endogenously processed and expressed on the target cells with HLA-A*0201 molecule and is recognized by the CTLs. These results indicate that this peptide derived from UBE2T may be available to apply the cancer vaccines for patients with UBE2T expressing tumors.

Homology Analysis of Antigen Peptides

The CTLs stimulated with UBE2T-A24-9-60 (SEQ ID NO: 1), UBE2T-A24-9-45 (SEQ ID NO: 2), UBE2T-A24-9-133 (SEQ ID NO: 4), UBE2T-A24-9-138 (SEQ ID NO: 6), UBE2T-A24-9-43 (SEQ ID NO: 11), UBE2T-A24-9-106 (SEQ ID NO: 12), UBE2T-A24-9-3 (SEQ ID NO: 13), UBE2T-A24-9-105 (SEQ ID NO: 15), UBE2T-A24-10-130 (SEQ ID NO: 17), UBE2T-A24-10-131 (SEQ ID NO: 19), UBE2T-A24-10-133 (SEQ ID NO: 20), UBE2T-A24-10-99 (SEQ ID NO: 21), UBE2T-A24-10-154 (SEQ ID NO: 22), UBE2T-A24-10-105 (SEQ ID NO: 23), UBE2T-A24-10-115 (SEQ ID NO: 24), UBE2T-A24-10-177 (SEQ ID NO: 25), UBE2T-A24-10-44 (SEQ ID NO: 27), UBE2T-A02-9-107 (SEQ ID NO: 29), UBE2T-A02-9-30 (SEQ ID NO: 30), UBE2T-A02-9-106 (SEQ ID NO: 32), UBE2T-A02-9-49 (SEQ ID NO: 36), UBE2T-A02-9-13 (SEQ ID NO: 38), UBE2T-A02-9-132 (SEQ ID NO: 41), UBE2T-A02-10-70 (SEQ ID NO: 48), UBE2T-A02-10-6 (SEQ ID NO: 49), UBE2T-A02-10-106 (SEQ ID NO: 51), UBE2T-A02-10-102 (SEQ ID NO: 52), UBE2T-A02-10-30 (SEQ ID NO: 53), UBE2T-A02-10-101 (SEQ ID NO: 55), UBE2T-A02-10-29 (SEQ ID NO: 56) and UBE2T-A02-10-38 (SEQ ID NO: 58) showed significant and specific CTL activity. This result may be due to the fact that the sequences of UBE2T-A24-9-60 (SEQ ID NO: 1), UBE2T-A24-9-45 (SEQ ID NO: 2), UBE2T-A24-9-133 (SEQ ID NO: 4), UBE2T-A24-9-138 (SEQ ID NO: 6), UBE2T-A24-9-43 (SEQ ID NO: 11), UBE2T-A24-9-106 (SEQ ID NO: 12), UBE2T-A24-9-3 (SEQ ID NO: 13), UBE2T-A24-9-105 (SEQ ID NO: 15), UBE2T-A24-10-130 (SEQ ID NO: 17), UBE2T-A24-10-131 (SEQ ID NO: 19), UBE2T-A24-10-133 (SEQ ID NO: 20), UBE2T-A24-10-99 (SEQ ID NO: 21), UBE2T-A24-10-154 (SEQ ID NO: 22), UBE2T-A24-10-105 (SEQ ID NO: 23), UBE2T-A24-10-115 (SEQ ID NO: 24), UBE2T-A24-10-177 (SEQ ID NO: 25), UBE2T-A24-10-44 (SEQ ID NO: 27), UBE2T-A02-9-107 (SEQ ID NO: 29), UBE2T-A02-9-30 (SEQ ID NO: 30), UBE2T-A02-9-106 (SEQ ID NO: 32), UBE2T-A02-9-49 (SEQ ID NO: 36), UBE2T-A02-9-13 (SEQ ID NO: 38), UBE2T-A02-9-132 (SEQ ID NO: 41), UBE2T-A02-10-70 (SEQ ID NO: 48), UBE2T-A02-10-6 (SEQ ID NO: 49), UBE2T-A02-10-106 (SEQ ID NO: 51), UBE2T-A02-10-102 (SEQ ID NO: 52), UBE2T-A02-10-30 (SEQ ID NO: 53), UBE2T-A02-10-101 (SEQ ID NO: 55), UBE2T-A02-10-29 (SEQ ID NO: 56) and UBE2T-A02-10-38 (SEQ ID NO: 58) are homologous to peptide derived from other molecules that are known to sensitize the human immune system. To exclude this possibility, homology analyses were performed for these peptide sequences using as queries the BLAST algorithm (Internet at ncbi.nlm.nih.gov/blast/blast.cgi), which revealed no sequence with significant homology. The results of homology analyses indicate that the sequence of UBE2T-A24-9-60 (SEQ ID NO: 1), UBE2T-A24-9-45 (SEQ ID NO: 2), UBE2T-A24-9-133 (SEQ ID NO: 4), UBE2T-A24-9-138 (SEQ ID NO: 6), UBE2T-A24-9-43 (SEQ ID NO: 11), UBE2T-A24-9-106 (SEQ ID NO: 12), UBE2T-A24-9-3 (SEQ ID NO: 13), UBE2T-A24-9-105 (SEQ ID NO: 15), UBE2T-A24-10-130 (SEQ ID NO: 17), UBE2T-A24-10-131 (SEQ ID NO: 19), UBE2T-A24-10-133 (SEQ ID NO: 20), UBE2T-A24-10-99 (SEQ ID NO: 21), UBE2T-A24-10-154 (SEQ ID NO: 22), UBE2T-A24-10-105 (SEQ ID NO: 23), UBE2T-A24-10-115 (SEQ ID NO: 24), UBE2T-A24-10-177 (SEQ ID NO: 25), UBE2T-A24-10-44 (SEQ ID NO: 27), UBE2T-A02-9-107 (SEQ ID NO: 29), UBE2T-A02-9-30 (SEQ ID NO: 30), UBE2T-A02-9-106 (SEQ ID NO: 32), UBE2T-A02-9-49 (SEQ ID NO: 36), UBE2T-A02-9-13 (SEQ ID NO: 38), UBE2T-A02-9-132 (SEQ ID NO: 41), UBE2T-A02-10-70 (SEQ ID NO: 48), UBE2T-A02-10-6 (SEQ ID NO: 49), UBE2T-A02-10-106 (SEQ ID NO: 51), UBE2T-A02-10-102 (SEQ ID NO: 52), UBE2T-A02-10-30 (SEQ ID NO: 53), UBE2T-A02-10-101 (SEQ ID NO: 55), UBE2T-A02-10-29 (SEQ ID NO: 56) and UBE2T-A02-10-38 (SEQ ID NO: 58) are unique and thus, there is little possibility, to our best knowledge, that these molecules raise unintended immunologic response to some unrelated molecule. In conclusion, we identified novel HLA-A*2402 or HLA-A*0201 epitope peptides derived from UBE2T. Furthermore, it was demonstrated that epitope peptides of UBE2T may be applicable for cancer immunotherapy.

INDUSTRIAL APPLICABILITY

The present invention provides new epitope peptides derived from UBE2T that may induce potent and specific anti-tumor immune responses and have applicability to a wide variety of cancer types. Such peptides can find use as peptide vaccines against diseases associated with UBE2T, e.g., cancer, more particularly, bladder cancer, breast cancer, cervical cancer, cholangiocellular carcinoma, CML, colorectal cancer, esophageal cancer, gastric cancer, diffuse-type gastric cancer, NSCLC, lymphoma, osteosarcoma, ovarian cancer, pancreatic cancer, prostate cancer, SCLC, soft tissue tumor and testicular tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. A composition for inducing a cytotoxic T lymphocyte (CTL) in a subject whose HLA antigen is HLA-A2, wherein the composition comprises a peptide consisting of the amino acid sequence selected from the group consisting of SEQ ID NOs: 48, 29, 30, 32, 36, 38, 41, 49, 51, 52, 53, 55, 56 and 58 in combination with an adjuvant effective to enhance an immune response.

2. A method for inducing an antigen-presenting cell (APC) with CTL inducibility, wherein the method comprises the step of contacting an APC expressing HLA-A2 with a peptide consisting of the amino acid sequence selected from the group consisting of SEQ ID NOs: 48, 29, 30, 32, 36, 38, 41, 49, 51, 52, 53, 55, 56, and 58.

3. A method for inducing a CTL, wherein the method comprises the step of co-culturing a CD8 positive T cell with an APC that presents on its surface a complex of an HLA-A2 and a peptide consisting of the amino acid sequence selected from the group consisting of SEQ ID NOs: 48, 29, 30, 32, 36, 38, 41, 49, 51, 52, 53, 55, 56 and 58.

* * * * *